US 11,484,254 B2

(12) United States Patent
Branch et al.

(10) Patent No.: US 11,484,254 B2
(45) Date of Patent: Nov. 1, 2022

(54) FLOATING PATELLA SENSOR, KNEE STABILIZER WITH SAME AND ROBOTIC KNEE TESTING APPARATUS WITH SAME

(71) Applicant: ERMI, Inc., Atlanta, GA (US)

(72) Inventors: Thomas P. Branch, Atlanta, GA (US); Shaun K. Stinton, Chamblee, GA (US); Edward Dittmar, Marietta, GA (US); Nathaniel K. deJarnette, Lilburn, GA (US); T. Christopher Madden, Atlanta, GA (US)

(73) Assignee: RoboDiagnostics LLC, Atlanta, GA (US)

( * ) Notice: Subject to any disclaimer, the term of this patent is extended or adjusted under 35 U.S.C. 154(b) by 177 days.

(21) Appl. No.: 15/356,660

(22) Filed: Nov. 20, 2016

(65) Prior Publication Data

US 2017/0143250 A1    May 25, 2017

Related U.S. Application Data

(60) Provisional application No. 62/258,191, filed on Nov. 20, 2015.

(51) Int. Cl.
| | | |
|---|---|---|
| *A61B 5/00* | (2006.01) | |
| *A61B 5/11* | (2006.01) | |
| *A61B 6/00* | (2006.01) | |
| *A61B 34/30* | (2016.01) | |

(52) U.S. Cl.
CPC .............. *A61B 5/4585* (2013.01); *A61B 5/11* (2013.01); *A61B 5/1121* (2013.01); *A61B 5/4528* (2013.01); *A61B 5/6884* (2013.01); *A61B 5/702* (2013.01); *A61B 6/00* (2013.01); *A61B 34/30* (2016.02)

(58) Field of Classification Search
None
See application file for complete search history.

(56) References Cited

U.S. PATENT DOCUMENTS

| | | | | |
|---|---|---|---|---|
| 4,534,364 | A * | 8/1985 | Lamoreux .............. | A61B 5/103 600/587 |
| 4,583,554 | A * | 4/1986 | Mittelman ........... | A61B 5/4533 600/587 |
| 4,583,555 | A * | 4/1986 | Malcom ................. | A61B 5/103 600/595 |
| 4,649,934 | A * | 3/1987 | Fraser .................. | A61B 5/1107 600/595 |
| 4,799,497 | A * | 1/1989 | Riley, II ................. | A61B 5/103 600/587 |
| 4,804,000 | A * | 2/1989 | Lamb ..................... | A61B 5/103 33/512 |

(Continued)

Primary Examiner — Sean P Dougherty
Assistant Examiner — Benjamin S Melhus
(74) *Attorney, Agent, or Firm* — Lempia Summerfield Katz LLC

(57) ABSTRACT

A joint manipulation and evaluation apparatus has a mechanism configured to manipulate a first bone of a joint relative to a second bone of the joint. The apparatus has a joint stabilizer arranged to engage the joint and hold the second bone in place as the first bone is manipulated. A sensor is coupled to the joint stabilizer and is configured and arranged to detect residual movement of a clamped portion of the joint relative to the joint stabilizer as the first bone is manipulated.

12 Claims, 12 Drawing Sheets

(56) References Cited

U.S. PATENT DOCUMENTS

| | | | | |
|---|---|---|---|---|
| 4,913,163 A | * | 4/1990 | Roger | A61B 5/4533 |
| | | | | 600/595 |
| 4,969,471 A | * | 11/1990 | Daniel | A61B 5/103 |
| | | | | 600/587 |
| 5,335,674 A | * | 8/1994 | Siegler | A61B 5/103 |
| | | | | 600/595 |
| 5,348,025 A | * | 9/1994 | Wolfe | A61B 5/1107 |
| | | | | 600/595 |
| 5,911,695 A | * | 6/1999 | Watkins | A61B 5/103 |
| | | | | 600/553 |
| 5,935,086 A | * | 8/1999 | Beacon | A61B 5/103 |
| | | | | 600/595 |
| 5,957,869 A | * | 9/1999 | Caruso | A61B 5/103 |
| | | | | 600/595 |
| 6,013,039 A | * | 1/2000 | Watkins | A61B 5/103 |
| | | | | 33/512 |
| 6,551,258 B1 | * | 4/2003 | Herling | A61B 5/103 |
| | | | | 600/595 |
| 2004/0260208 A1 | * | 12/2004 | Laprade | A61B 5/1071 |
| | | | | 600/595 |
| 2007/0055176 A1 | | 3/2007 | Branch et al. | |
| 2009/0124936 A1 | | 5/2009 | Branch et al. | |
| 2009/0264797 A1 | * | 10/2009 | Mayr | A61B 5/1071 |
| | | | | 600/595 |
| 2011/0213275 A1 | * | 9/2011 | Boos | A61B 5/11 |
| | | | | 600/595 |
| 2012/0046540 A1 | | 2/2012 | Branch et al. | |
| 2014/0081181 A1 | | 3/2014 | Branch et al. | |
| 2015/0032034 A1 | * | 1/2015 | Petrigliano | A61B 5/4585 |
| | | | | 600/595 |

\* cited by examiner

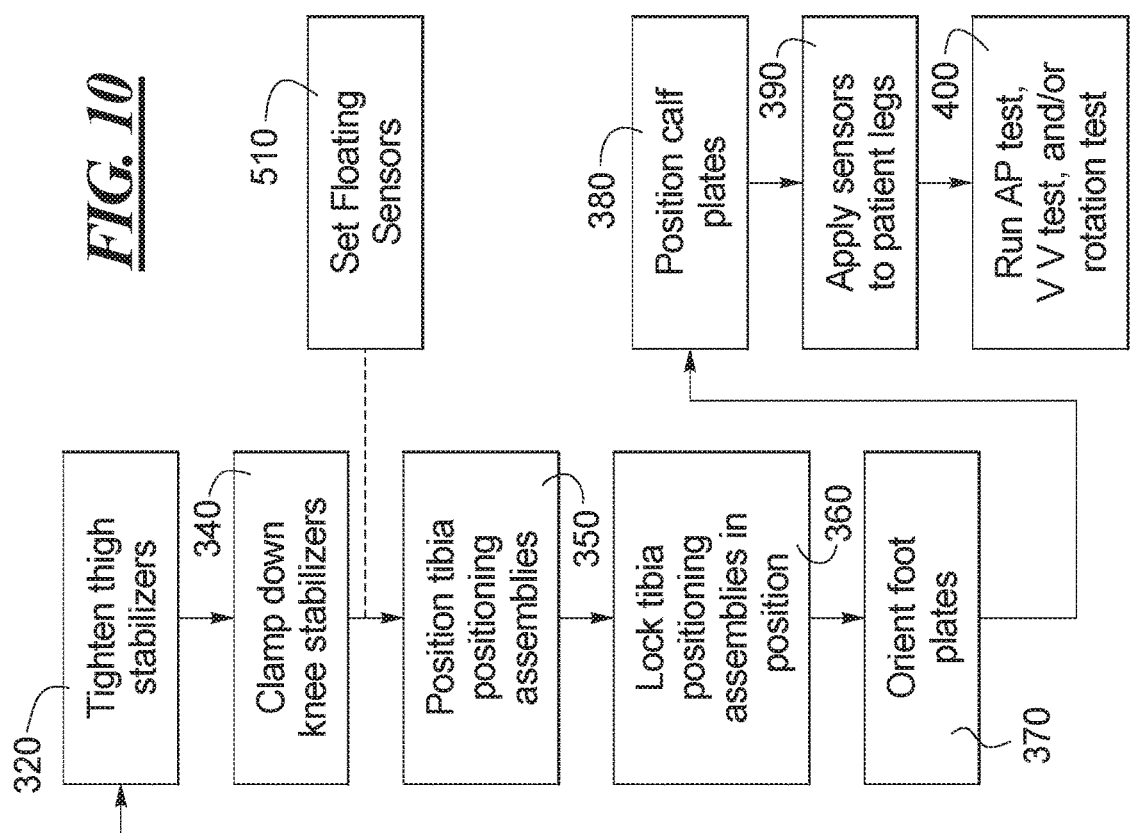
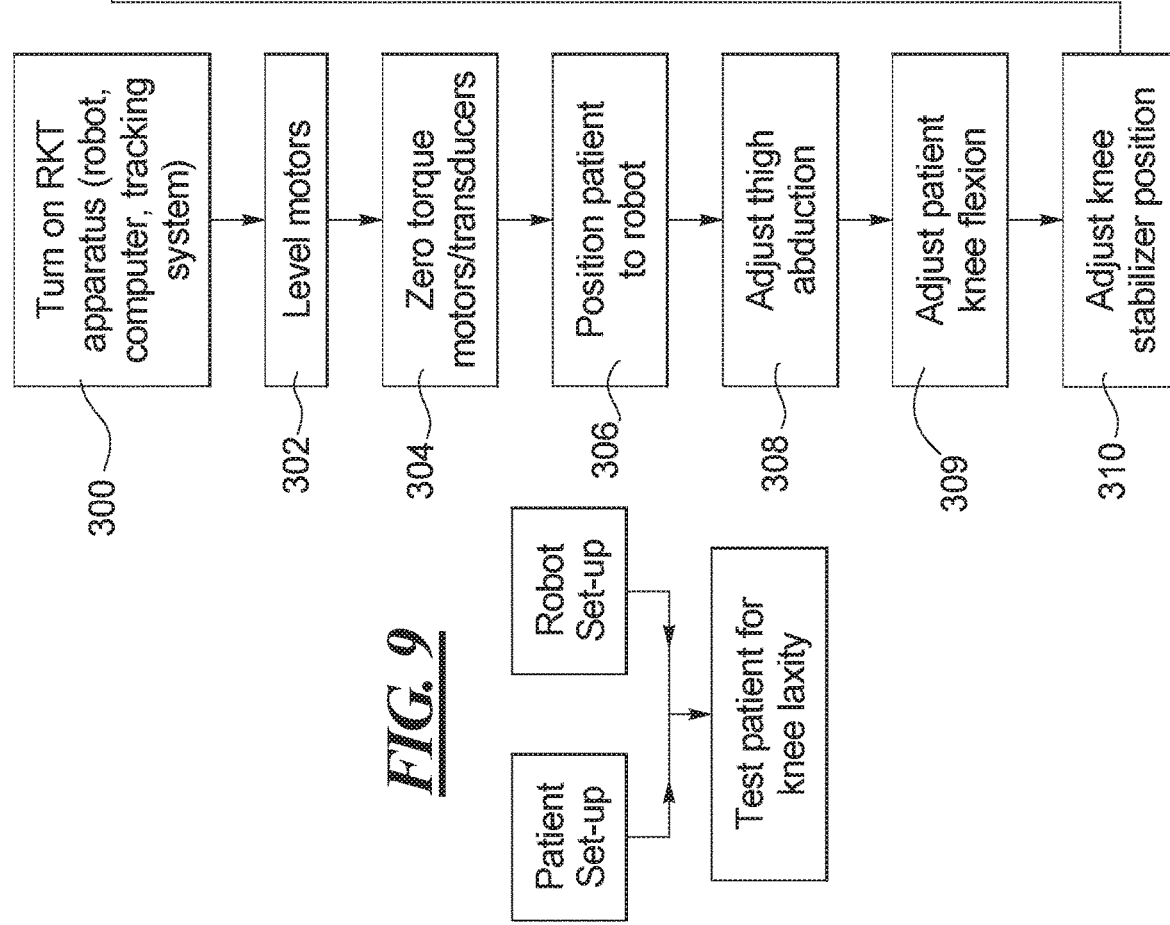

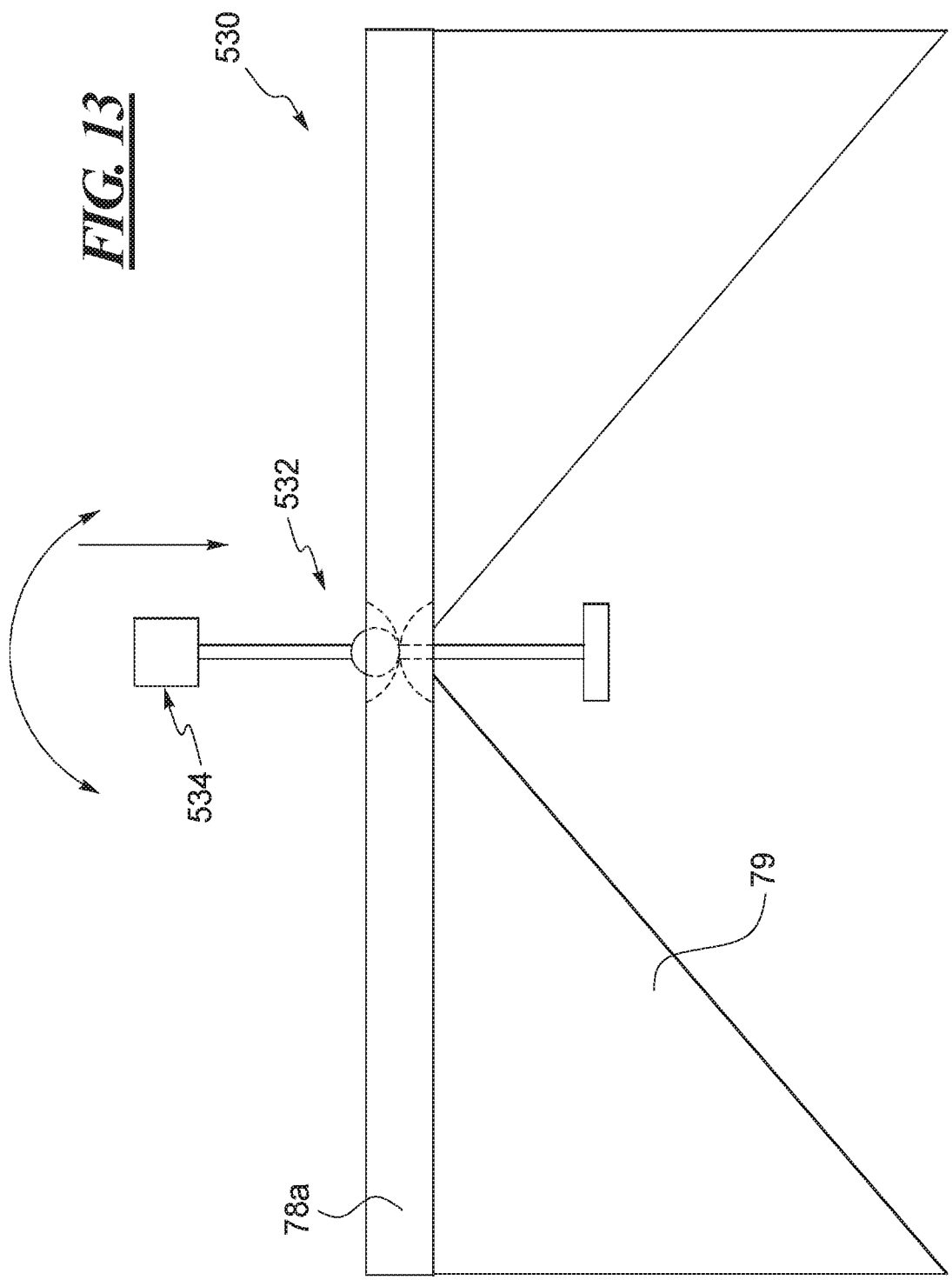

FLOATING PATELLA SENSOR, KNEE STABILIZER WITH SAME AND ROBOTIC KNEE TESTING APPARATUS WITH SAME

RELATED APPLICATION DATA

This patent is related to and claims priority benefit of U.S. Provisional Application Ser. No. 62/258,191 filed on Nov. 20, 2015 and entitled "Floating Patella Sensor, Knee Clamp with Floating Patella Sensor, and Robotic Knee Testing Device with Same." The entire contents of this prior filed application are hereby incorporated herein by reference.

BACKGROUND

1. Field of the Disclosure

The disclosure generally relates to a joint manipulation and evaluation apparatus, and more particularly to a floating sensor for a joint stabilizer of such an apparatus.

2. Description of Related Art

The knee joint is composed of the femur or thigh bone, the tibia or shin bone, and the patella or knee cap. The bones are connected by fibrous structures called ligaments, which allow a certain amount of "joint play" or motion to exist between the bone structures. When this joint play is increased, or decreased, an abnormal or pathological condition exists in the knee. Attempts have been made in the past to quantify this increase or decrease in joint play of the knee with limited success.

Knee injuries often cause damage to one or more of the structures that form the knee joint. Such injuries typically cause an increase in joint play or motion of the knee. A patient may interpret an increase in joint play as a sensation that the knee is slipping or coming out of joint. In other words, this sensation may be described by the patient as the feeling of joint instability. Knee instability may be related in part to an increase in the length of the ligaments that connect the bones together, an increase or change in compliance (elastic resilience or stretchiness) of the ligaments, or both. Knee instability may also be related in part to the shape and size of the joint bones. The degree or likelihood of the knee joint bones coming out of joint or becoming unstable is related to the amount of stretch or increased length of each knee ligament, the number of knee ligaments involved, and the existence of damage to one or more other support structures of the knee joint, such as the joint bones themselves, the menisci, or the like. Accurate measurement of an increase in ligament length can be critical to restoring a patient's injured or damaged knee to as close as possible to its original functional and anatomical structure and condition.

For the most part, knee injuries and ligament damage have been diagnosed using only manual tests. These tests are performed by doctors or other medical personnel, i.e., clinicians, on the patient in order to detect and measure joint play to diagnose damage to the knee ligaments or other knee joint support structures. There are several commonly known manual tests used to evaluate increased joint play, which is usually associated with an anterior cruciate ligament (ACL) tear. These tests include the Lachman's test, the Pivot Shift test, and the Anterior Drawer Test. Because these tests are performed manually by individual medical personnel, these tests naturally are limited by the specific clinician's subjective evaluation. The subjective nature of the tests may hinder the precision or accuracy of any diagnosis of the extent of ligament lengthening, the change in ligament compliance or elastic resilience, i.e., stretchiness, or both.

The Lachman's test is performed with a patient lying in a supine position. The clinician will bend the patient's knee joint at approximately 20 to 30 degrees. The clinician places one hand on the patient's upper thigh and their other hand below the upper part of the patient's calf. The clinician then applies upward pressure under the patient's calf and downward pressure on the patient's thigh. This induces a translation between the patient's femur and tibia. The degree of translation is subjectively determined by the clinician to diagnose the injury or joint damage.

The Pivot Shift test is similarly performed with the patient lying in a supine position. The leg is straightened out so that the knee joint is placed in full extension (x-axis rotation). A valgus or side-to-side outward rotation (y-axis rotation) force and an internal or twisting rotation (z-axis rotation) force is applied to the knee to allow the lateral tibia to slip anteriorly from underneath the lateral femoral condyle. As the knee is flexed or bent (x-rotation), the tibia is allowed to slip suddenly back underneath the femoral condyle. The clinician subjectively determines whether there is an abnormal external rotation (z-axis rotation) and posterior translation (y-axis translation) of the tibia with respect to the femur. The degree of shift that is felt or determined by the clinician represents to the clinician the relative increased translation (y-axis translation) of the lateral side of the knee with respect to the increased translation (y-axis translation) of the medial side of the knee. A sudden shift in the knee joint is felt by the clinician and represents the point at which the tibia bone slides from in front of the radius of curvature of the curved end of the femur back to its normal position under the femoral condyle. The clinician then subjectively rates the pivot shift as Grade I, Grade II, or Grade III depending upon the degree of rotational and translational shift felt during the test. The Pivot Shift test is inherently subjective, difficult to accurately perform, difficult to teach, and ultimately difficult to quantify.

The Anterior Drawer test is also performed with the patient lying in a supine position, but with the knee joint bent to about 90 degrees (x-axis rotation). The patient's foot is supported by a table or chair while the clinician applies thumb pressure to the knee joint. The Anterior Drawer test is subjectively graded by the clinician based on the perceived amount or extent of anterior translation of the tibia with respect to the femur. A Grade I injury is determined as having about 5 mm or less of anterior translation. A Grade II injury is determined as having between about 6 to 10 mm of anterior translation. A Grade III injury is determined as having between about 11 to 15 mm of anterior translation.

For a clinician to diagnose an injured ACL using the aforementioned manual tests, the clinician must determine whether the knee feels "abnormal." The accuracy of an ACL injury diagnosis provided by a clinician using currently known manual tests depends on the skill and experience of the clinician and their subjective determinations. A misdiagnosis can lead to unnecessary treatment or unnecessary delay in treatment, which may result in an increased risk for further injury or damage to the patient's knee joint.

There are also manual tests for the lateral collateral ligament (LCL), medial collateral ligament (MCL), and posterior cruciate ligament (PCL). Each manual test relies on grading the degree of length increase in the ligament based on relative increase in joint play into three Grades or categories. There is no effort to grade the compliance or elastic resilience, i.e., stretchiness, of the ligaments using these manual tests. However, an expert clinician may describe the ligament in terms of its subjective feel to the clinician. Also, a knee joint may have injury or damage to more than one ligament or structure. The more ligaments and structures of the knee joint that are damaged, the more complex it is for the clinician to perform a manual knee examination. This can make the diagnosis less accurate and less precise.

Clinicians and surgeons manually examine the injured knee joint for altered or increased joint play. However, due to the variability in size of the patient, size and experience of the surgeon, and the potential degree or subtlety of an injury, consistent and reproducible reports of joint play between surgeons is not possible. Many reports have documented that, whether diagnosis is performed manually or even with manual arthrometers, the manual application of torque to the knee joint varies widely between clinicians. This results in inconsistencies in the examination of joint play.

Others have attempted to reduce the manual nature of such joint tests and to instrument the knee joint during testing. The objective has been to mechanically or objectively quantify or measure a change in the structure of the knee after ligament damage. Several devices have been developed in attempting to more accurately quantify the extent of injury or relative displacement and compliance of a ligament in the knee. In one example, such devices have been developed by Medmetric Corp. These devices include the KT-1000 and KT-2000 models (hereinafter "KT"). The KT devices are intended to measure the anterior-posterior translation of the tibia with respect to the femur along the y-axis. The KT devices attach to the patient's tibia during testing.

The KT devices attempt to quantify the findings achieved by a clinician performing the Lachman's test and the Anterior Drawer Test. Force is applied to a handle on the device, which measures the force and delivers the amount of applied force to the clinician using sounds, such as a low-pitched sound for a 15-pound force and a higher pitched sound for a 20-pound force. The applied force in the KT devices pulls anteriorly along the y-axis through a strap that wraps underneath the patient's calf. The translation is determined using a technique that measures the relative motion between a pad placed against the anterior tibia and a pad placed against the patella. The KT devices do not measure relative displacement or compliance in any of the other degrees of freedom in the knee. Also, quantified results from using the KT devices have not been correlated with patient satisfaction. In contrast, the subjective Pivot Shift test has been correlated with patient satisfaction.

Other devices are also known and include the Stryker KLT, the Rolimeter, and the KSS system. These known devices use similar mechanisms to attempt to quantify the normal amount of joint play or motion between the femur and tibia in the knee joint, as well as any increased joint play or motion in the joint associated with ligament lengthening and damage. The applicant of the instant application has developed robotic knee testing (RKT) apparatuses, the basics of which are disclosed and described in U.S. publication nos. 2012/0046540 and 2014/0081181. Each apparatus, in part, utilizes motors to perform knee movements during testing and employs sensors to measure degree of relative movement of the structures in the knee joint. Portions of the knee and leg can be stabilized or moved, as needed during testing.

Non-invasive evaluation systems sometimes utilize sensors or markers that are attached to the skin. These types of sensors and systems can include, but are certainly not limited to, optoelectronic, ultrasonic, and electromagnetic motion analysis systems. The skin sensors or markers are merely representations of location of the underlying bones. However, numerous published reports have documented significant measurement error related to skin artifact with such systems. To avoid the inaccuracies associated with skin artifact, medical imaging systems may be utilized to precisely determine the position/location of the bones accurately. However, sometimes, medical imaging systems are not a viable option, such as for testing and evaluating joint play utilizing various joint play manipulation and evaluation devices and apparatuses.

SUMMARY

Accordingly, there is a need for an improved, i.e., accurate, objective, reliable and/or reproducible measure of the impact of damage or injury to the knee, as well as other joints. Such injuries or damage to the knee can be to the ACL as well as other ligaments and structures in the knee or combination of ligaments and other structures in the knee. The improved measure can be used in the clinical setting on patients. For example, since an injury to the ACL produces both an increase in anterior translation (y-axis translation) and rotation (z-axis rotation), an objective measure of these changes would both aid in the diagnosis of the injury and aid in verifying restoration of the joint after ligament reconstruction surgery. Also, the improved measurement of displacement and compliance around different degrees of freedom in the knee would help objectively describe the individual and complex changes to 'joint play' that occur in an injured knee with structural damage. A need exists for systems and methods that can provide accurate, reproducible and objective data on the changes in 'joint play' or motion that occur with an injured knee compared to a healthy knee. The improved systems and methods can also provide data that can be compared to data from the general population. As a result, the clinician can achieve patient satisfaction with focused, biomechanical, and proven surgical interventions specific to a given injured joint, and for that knee or joint to be compared across an entire data set of damaged knees or joints.

A need also exists for systems, methods, and apparatuses, which accommodate variances of patient body structure. It is well understood that each human body is different and may require particular attention when being treated and/or analyzed or evaluated. This may be particularly evident in the case of abnormalities in bones, tendons, joints, and the like due to injury or damage. A need also exists for systems, methods, and apparatuses that can provide the type of accurate, reproducible, and objective data described above without inherently and/or indirectly adversely impacting the accuracy, reproducibility, and/or objectiveness of the tests and measured data acquired.

In one example, according to the teachings of the present disclosure, a joint manipulation and evaluation apparatus has a mechanism configured to manipulate a first bone of a joint relative to a second bone of the joint. A joint stabilizer is arranged to engage the joint and hold the second bone in place as the first bone is manipulated. A sensor is coupled to the joint stabilizer and configured and arranged to detect residual movement of a clamped portion of the joint relative to the joint stabilizer as the first bone is manipulated.

In one example, the sensor can have a joint contacting end positioned to contact the clamped portion of the joint. The joint contacting end can detect the residual movement of the clamped portion.

In one example, the joint stabilizer can be a knee stabilizer, the joint can be a knee joint, the second bone can be a femur of the knee joint, the first bone can be a tibia of the knee joint, and the clamped portion can be a patella of the knee joint.

In one example, the joint manipulation and evaluation apparatus can include a first drive configured to manipulate the first bone relative to the second bone in a first direction, a second drive configured to manipulate the first bone relative to the second bone in a second direction, and a third drive configured to manipulate the first bone relative to the second bone in a third direction. The first, second, and third directions can be different relative to each other.

In one example, the joint stabilizer can have a frame arranged to surround the joint.

In one example, the joint stabilizer can have a frame arranged to surround the joint and can have one or more pads carried within the frame. The pads can be positioned so as to be disposed between the frame and the joint.

In one example, the sensor can be an electromagnetic sensor carried on a frame of the joint stabilizer. The sensor can be movable relative to the joint stabilizer or have a portion that is movable relative to the joint stabilizer.

In one example, the sensor can have a joint contacting end positioned within a frame of the joint stabilizer. The joint contacting end can be being movable relative to the frame.

In one example, the sensor can have a joint contacting end. The joint contacting end can be movable along only a single linear axis relative to a frame of the joint stabilizer.

In one example, the sensor can have a joint contacting end. The joint contacting end can be movable along at least one linear axis relative to the frame and pivotable about a pivot point relative to the frame.

In one example, the joint manipulation and evaluation apparatus can include a processor, a memory device, or both coupled to the sensor. The processor, memory device, or both can be configured to receive and/or store data signals from the sensor that corresponding to the residual movement.

In one example, the joint manipulation and evaluation apparatus can include a processor coupled to the sensor. The processor can be programmed to evaluate the joint and to account for the residual movement of the clamped portion in the evaluation of the joint.

In one example, according to the teachings of the present disclosure, a joint stabilizer is configured for use with a joint manipulation and evaluation apparatus. The joint stabilizer has a frame configured to clamp onto a human joint and hold a second bone of the human joint in place as a first bone of the human joint is manipulated. A sensor is coupled to the joint stabilizer. The sensor is configured and arranged to detect residual movement of a clamped portion of the human joint relative to the frame as the first bone is manipulated.

In one example, the joint stabilizer can include one or more pads carried within the frame. The pads can be positioned so as to be disposed between the frame and the human joint.

In one example, the sensor can be an electromagnetic sensor carried on the frame. The sensor or a portion of the sensor can be movable relative to the frame.

In one example, the sensor can have a joint contacting end. The joint contacting end can be positioned within the frame and can be movable relative to the frame.

In one example, the sensor can have a joint contacting end. The joint contacting end can be movable along only a single linear axis relative to the frame.

In one example, the sensor can have a joint contacting end. The joint contacting end can be slidable along a single linear axis.

In one example, the sensor can have a joint contacting end. The joint contacting end can be movable relative to multiple axes, movable in a plurality of different directions, or both.

In one example, the human joint can be a knee joint and the clamped portion can be a patella of the knee joint.

In one example, the joint stabilizer can be a knee stabilizer, the joint can be a knee joint, the second bone can be a femur of the knee joint, the first bone can be a tibia of the knee joint, and the clamped portion can be a patella of the knee joint.

In one example, the sensor in either the aforementioned joint manipulation and evaluation apparatus or the joint stabilizer can be a linear actuator. The linear actuator can be carried on a frame of the joint stabilizer and can be movable relative to the joint stabilizer.

In one example, according to the teachings of the present disclosure, a method of detecting residual movement in a joint during manipulation and evaluation of the joint includes positioning a joint of a patient adjacent a joint stabilizer, wherein the joint stabilizer has a sensor coupled thereto. The sensor has a portion in contact with part of the joint. The method includes securing the joint stabilizer to a clamped portion of the joint so as to engage the joint and hold a second bone of the joint in place. The method includes manipulating a first bone of the joint relative to the second bone. This step can include utilizing a robotic knee testing apparatus that incorporates the joint stabilizer. The method includes detecting residual movement of the clamped portion of the joint relative to the joint stabilizer as the first bone is manipulated.

BRIEF DESCRIPTION OF THE DRAWINGS

Objects, features, and advantages of the present invention will become apparent upon reading the following description in conjunction with the drawing figures, in which:

FIG. 9 shows a flow chart of one example of a set-up and knee laxity test method according to the teachings of the present disclosure.

FIG. 10 shows a flow chart depicting additional steps for each of the patient set-up and robot set-up steps of FIG. 9.

FIG. 13 shows an upper portion of an alternative example of a knee stabilizer with a patella sensor constructed in accordance with the teachings of the present disclosure.

DETAILED DESCRIPTION OF THE DISCLOSURE

The disclosed floating patella sensor, knee or patellar stabilizer, and robotic knee testing (RKT) apparatus (i.e., one form of a joint manipulation and evaluation apparatus) solve or improve upon one or more of the above noted and/or other problems and disadvantages with prior known knee testing devices. In particular, the disclosed knee stabilizer and RKT apparatus utilize a floating sensor that determines the degree of residual femur movement during knee testing while the femur and patella are held in place by the knee stabilizer. The floating sensor can be connected to a processor of the RKT apparatus or an external computer. Data obtained by the floating sensor related to such residual movement of the femur and patella can then be used within the processor to account for such residual movement in the diagnosis of the knee joint. The disclosed floating sensor, stabilizer, and evaluation apparatus can also be further developed and used to evaluate joints other than knee joints, such as elbow joints, shoulders, ankles, wrists, and the like. The RKT apparatus can thus alternatively be another type of joint manipulation and evaluation apparatus.

One objective of the disclosed RKT apparatus is to provide a controlled application of torque during joint examination, with the magnitude, direction, and rate of torque application being controlled and with residual patella movement being accounted for during the evaluation. The disclosed RKT apparatus produces superior results by doing so. These and other objects, features, and advantages of the disclosed floating sensor, knee stabilizer, and RKT apparatus will become apparent to those having ordinary skill in the art upon reading this disclosure.

Figure 1:
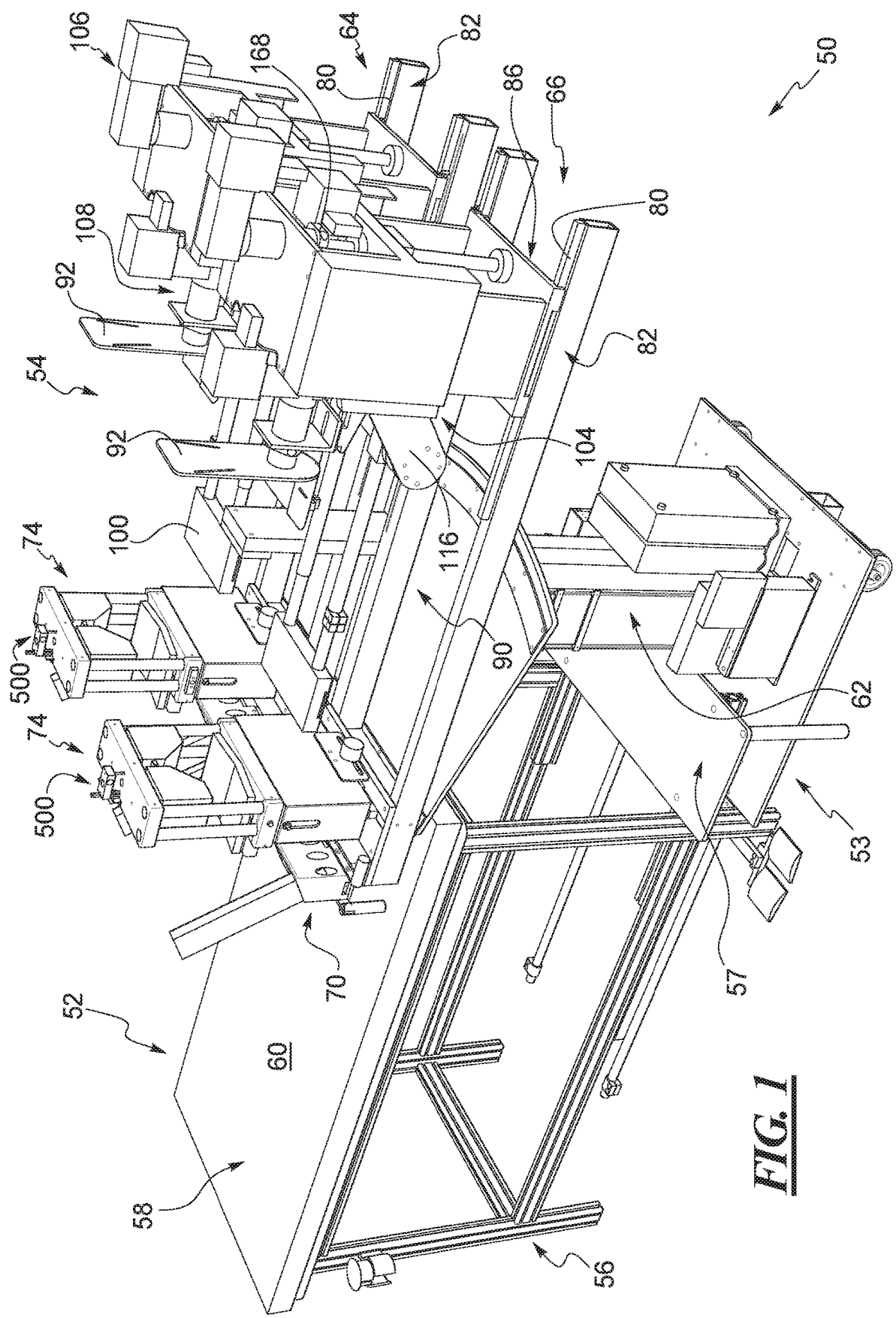
FIG. 1 shows a perspective view of one example of a robotic knee testing apparatus according to the teachings of the present disclosure.

Turning now to the drawings, FIG. 1 shows one example of a RKT apparatus 50 that has been developed by the applicant and assignee of the present inventions that are disclosed and described herein. Specific details of the RKT apparatus 50 are more fully disclosed and described in the above-noted U.S. publication no. 2014/0081181 ("181"), which is owned by the applicant and assignee of the inventions disclosed herein. Specific details of the overall function and operation of the robotic portion of the RKT apparatus are described in the '181 publication and in the above-noted U.S. publication no. 2012/0046540, which is also owned by the applicant and assignee of the inventions disclosed herein. Further details of the specific embodiment of the RKT apparatus 50 shown and described herein are described in co-pending U.S. application Ser. No. 15/601, 410 (published as U.S. publication no. 2018/0333318 and entitled "Positioning System for Robotic Knee Testing Apparatus and Method of Using Same"). The entire contents of both the '181 and '540 publications, and the '318 publication, are hereby incorporated herein by reference.

Figure 2:
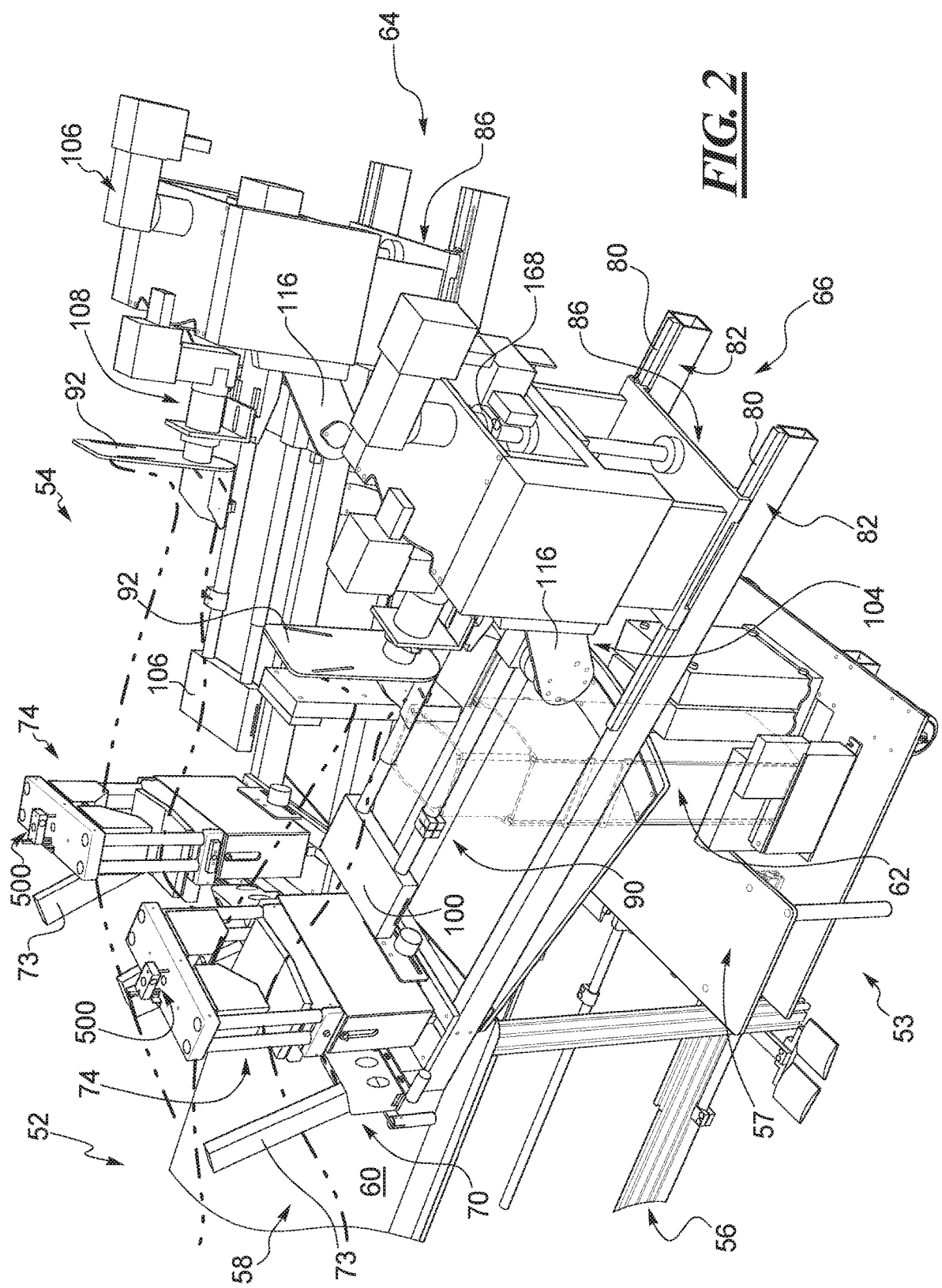
FIG. 2 shows an enlarged view of the joint manipulation mechanism or robot of the robotic knee testing apparatus of FIG. 1 and depicts left and right legs of a patient positioned relative to left and right leg portions of the robot.

The RKT apparatus 50 of FIG. 1 generally has a patient support, i.e., a table assembly 52. The RKT apparatus 50 also has a robotic device or limb or joint manipulation mechanism, identified for ease of description herein as a robot 54, positioned at one end or edge of the table assembly 52. The robot 54 is supported by a robot positioning system 53 that is configured so that the robot is movable relative to the table assembly 52. The table assembly 52 in this example has a supporting frame that is identified herein as a base 56 beneath a patient platform 58. The base 56 is configured to rest on a floor or surface and to support the patient platform 58 above the floor. The patient platform 58 can include a substantially rigid or sturdy panel (not shown) capable of holding and supporting a patient thereon. The panel can be affixed to or otherwise supported by the base 56. The panel of the patient platform 58 can underlie a padded surface 60, which can include a textile or fabric material that covers a cushion, padding, or the like (also not shown). As shown in FIGS. 1 and 2, the patient support can include a step 57 positioned at the distal end of the table assembly 52 to assist a patient to step up onto the patient platform 58.

As will be evident to those having ordinary skill in the art, the configuration and construction of the table assembly 52, robot positioning system 53, and step 57 can vary considerably from the example disclosed, illustrated, and briefly described herein. The robot positing system 53, base 56, the patient platform 58, and step 57 can each be altered in configuration, size, shape, orientation, height, construction, materials, and the like. The patient support need not be a table, but instead can be a chair, a suspension system, or other suitable structure that is capable of properly positioning and retaining a patient relative to the robot 54 for testing and examination or evaluation. The table assembly 52, robot positioning system 53, and/or step 57 can further include additional features, though not disclosed or described herein, that may be used to assist in the patient sitting on the patient platform, to assist in positioning a patient on the patient platform, to assist in maintaining a patient's position on the platform, or to otherwise enhance patient comfort or improve performance of the table assembly, the RKT apparatus, or both.

The positioning system 53 of the RKT apparatus 50 can be configured to allow moving the robot 54 relative to the table assembly 52. The positioning system 53 is adjustably connected to the table assembly 52 in this example. The positioning system 53 has a column lift 62 that can raise and lower the robot 54 as well. Details of the positioning system 53 are not described herein. In this example, the positioning system 53 may be configured to further assist a patient in getting onto the patient platform 58, as well as to aid in positioning the patient for testing.

Figure 3:
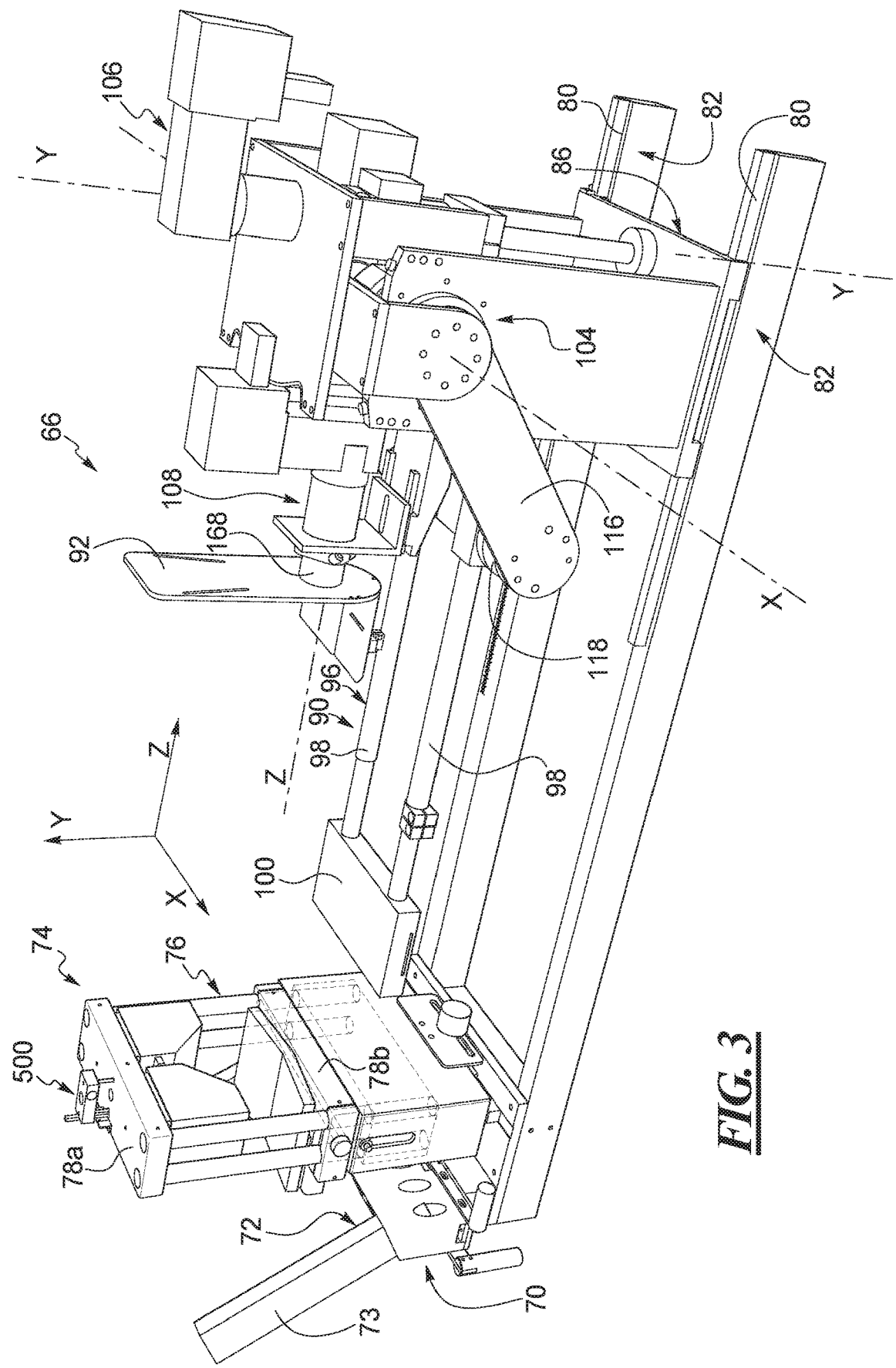
FIG. 3 shows a right leg portion of the robot of FIG. 2 and depicts an X-Y-Z coordinate system defined by the right leg portion.

In the disclosed example, as shown in FIGS. 2 and 3, the robot 54 has a left leg testing and evaluation mechanism and a right leg testing and evaluation mechanism, each mechanism respectively identified herein as a left leg portion 64 and a right leg portion 66 of the robot. The left and right leg portions 64, 66 have substantially the same construction, and may be essentially identical, if desired. Each is also constructed to support and evaluate a left leg and right leg, respectively, of a patient. Therefore, like reference numerals are used herein to identify common parts of each of the two leg portions 64, 66 that have the same construction.

The left and right leg portions 64, 66 each have a sub-frame 68 that, in this example, is supported directly or indirectly by the robot positioning system 53. Each sub-frame 68 supports the components and parts of the corresponding left and right leg portions 64, 66. For ease of description, the right leg portion 66 of the robot 54 is described in some detail below with the understanding that the left leg portion 64 has or may have the same overall construction. Differences between the two leg portions may be identified herein, if and as needed. It is possible that an RKT apparatus may have only one leg portion for evaluating only one leg of a patient at a time. However, in the disclosed example, the RKT apparatus 50 has left and right leg portions 64, 66.

Figure 4:
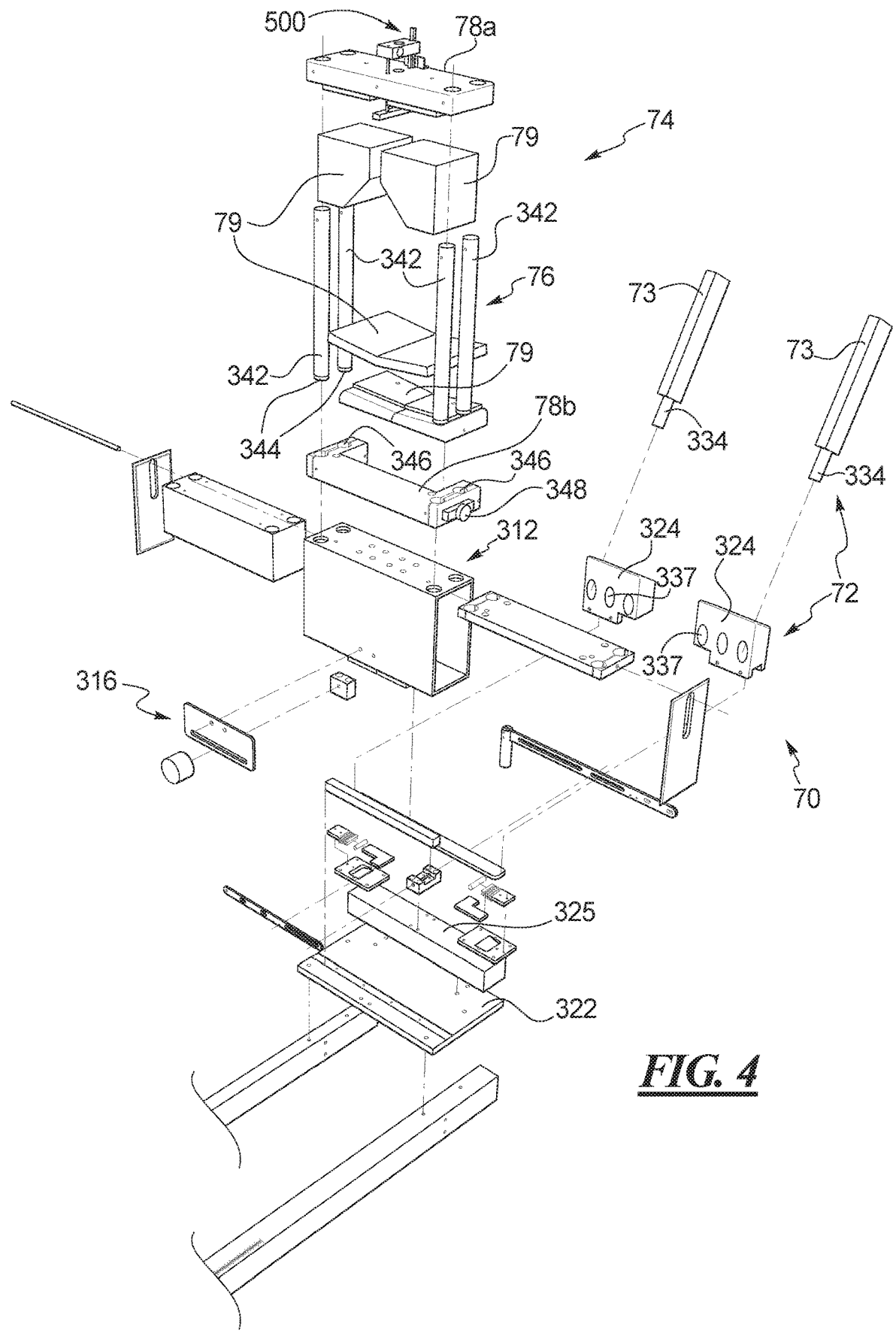
FIG. 4 shows an exploded view of a thigh immobilizer and a knee stabilizer of the right leg portion of FIG. 3.
Figure 5:
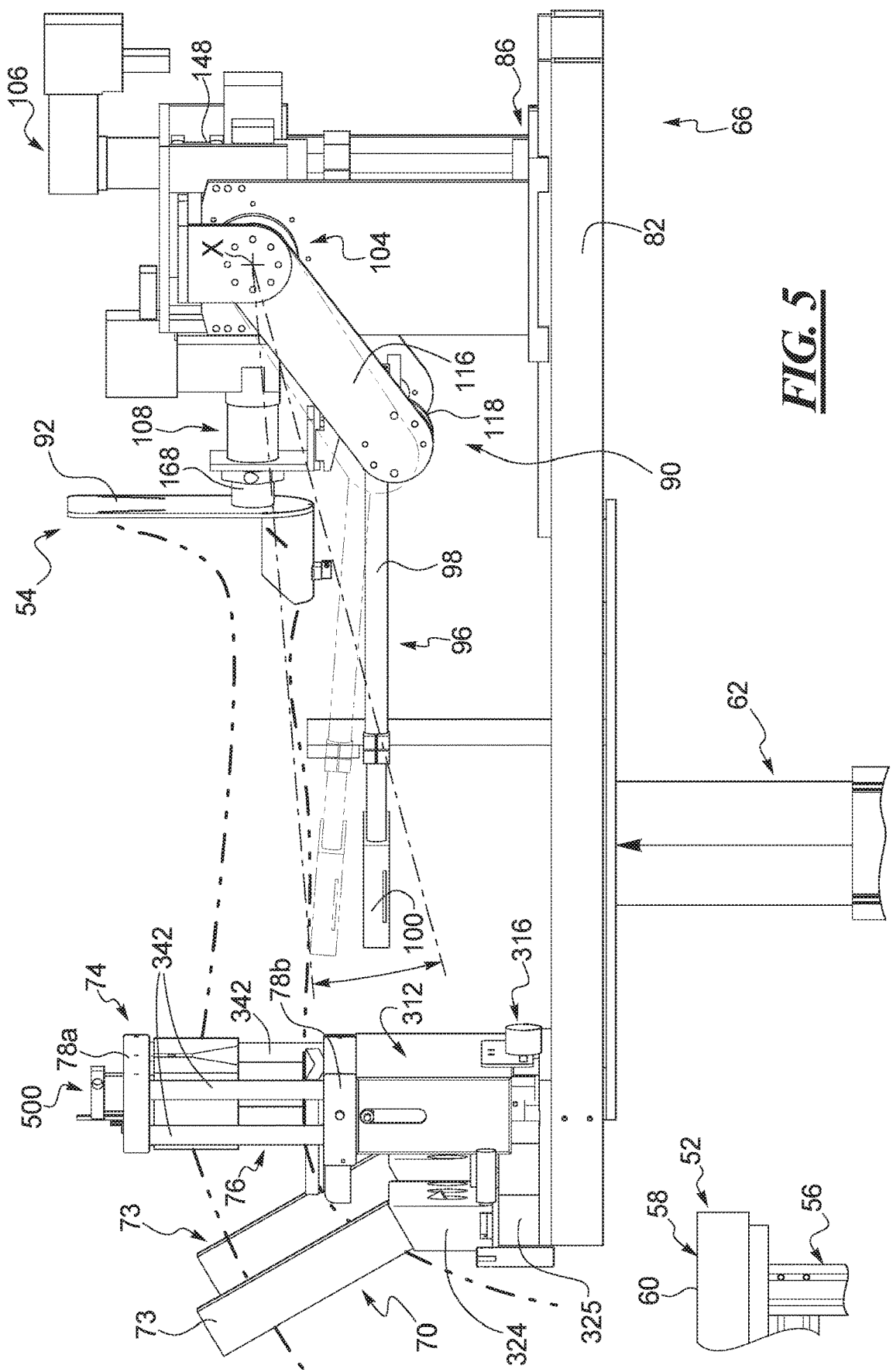
FIG. 5 shows a side view of the robot of FIG. 2 as viewed from the right leg portion side of the robot and illustrates anterior-posterior motion about the X-axis of a tibia positioning assembly of the right leg portion.

As depicted in FIGS. 3-5, the right leg portion 66 has a thigh clamp or immobilizer 70 positioned closest to the table assembly 52. The thigh immobilizer 70 can be mounted to the robot positioning system 53 or the sub-frame 68, or can be otherwise mounted to a portion of the RKT apparatus 50 in a manner suitable for use as described below. The thigh immobilizer 70 can be constructed to be adjustable in clamping width and in lateral position to accommodate a wide range of patients of different size and body type. The thigh immobilizer 70 should be positioned or positionable to contact a portion of a patient's upper leg or thigh above the knee.

The thigh immobilizer 70 in this example has a pair of femur clamping elements 72, i.e., medial and lateral clamping elements that are laterally spaced apart and width-wise adjustable relative to one another. Though not shown herein, the clamping elements 72 can include a pad or pads on the thigh facing surfaces, if desired, to provide a degree of comfort for a patient. The femur clamping elements 72 can be side-to-side adjusted relative to one another in order to clamp or otherwise securely hold a patient's right femur and thigh in a substantially fixed side-to-side position during testing, evaluation, or treatment, as described below. The configuration and construction of the thigh immobilizer 70 can vary considerably from the example shown herein. The clamping elements 72 can be replaced by other suitable securing or clamping devices or elements and the mechanisms to adjust and secure the thigh immobilizer 70 can also vary.

In the example shown in FIGS. 3-5, the right leg portion 66 also has a knee stabilizer 74 positioned adjacent the thigh immobilizer 70. The knee stabilizer 74 can also be mounted to the robot positioning system 53 or the sub-frame 68, or can be otherwise mounted to a portion of the RKT apparatus 50 in a manner suitable for use as described below. The knee stabilizer 74 can be constructed to be adjustable in clamping height and in lateral position to accommodate a wide range of patients of different size and body type. The knee stabilizer 74 should be positioned or positionable to contact the knee or patella at the lower end of a patient's femur and thigh, as depicted in FIG. 5.

The knee stabilizer 74 acts as a knee stabilizer or patellar clamp and can include a framework 76 arranged to surround and clamp onto a patient's joint or knee. The knee stabilizer 74 in this example has a pair of patellar clamping elements 78a, 78b that are vertically spaced apart and adjustable relative to one another along the framework 76. The patellar clamping elements 78a, 78b can be vertically adjusted in order to clamp or otherwise securely hold the lower end of a patient's right femur and patella in a substantially fixed vertical position during testing, evaluation, or treatment, as described below. The knee stabilizer 74 should also be capable of being secured in a fixed selected lateral position, once properly adjusted for a given patient, relative to the table assembly 52 and/or robot 54 during testing. The configuration and construction of the knee stabilizer 74 can vary considerably from the example shown herein. The patellar clamping elements 78a, 78b can be replaced by other suitable securing or clamping devices or elements and the mechanisms to adjust and secure the knee stabilizer 74 can also vary.

The knee stabilizer 74 can include a plurality of substantially rigid and/or resilient pads 79, such as on the upper and lower patellar clamping elements 78. The pads 79 can be configured and arranged to lie adjacent the patient's knee, preventing the framework 76 and the patellar clamping elements 78a, 78b, respectively, from directly contacting the patient's knee. The pads 79 can be solid, hollow, pressurized, hydraulically filled, pneumatically filled, or the like and can be rubber, foam, or otherwise formed of suitable materials. In one example, the pad or pads 79 on the upper patellar clamping element 78a can be configured to define a V-shape within the framework 76. The patient's leg can then be captured within the V-shape as the upper and lower patellar clamping elements 78a, 78b are drawn toward one another to capture and hold still the patient's leg during a procedure.

The thigh immobilizer 70 and/or the knee stabilizer 74 may be mechanically adjustable to manually fit and accommodate different sized patients. In one alternative, the thigh immobilizer 70 and/or the knee stabilizer 74 may be electrically operable to adjust the femur clamping elements 72, the patellar clamping elements 78a, 78b, respectively, or both. In another alternative example, the femur clamping elements 72 and/or the patellar clamping elements 78a, 78b may be pneumatically or hydraulically operable to adjust the thigh immobilizers 70 and knee stabilizers 74. In yet another alternative, the thigh immobilizer 70, the knee stabilizer 74, or both, may include two or more such systems or mechanisms for adjusting the respective clamping elements.

The thigh immobilizer 70 and/or femur clamping elements 72 and the knee stabilizer 74 and/or framework 76 and patellar clamping elements 78a, 78b can be formed of metal, plastic, or other suitable materials. The thigh and knee stabilizers 70 and 74 can vary in shape, configuration and construction, as desired. The thigh immobilizers 70 and knee stabilizers 74, in combination, are intended to secure a patient's leg to hold the femur and patella in a vertically (knee stabilizer) and laterally (thigh stabilizer) substantially fixed position during a test, evaluation, or treatment cycle. Features and aspects of the disclosed thigh immobilizers 70 and knee stabilizers 74 can vary considerably while accomplishing this objective.

In this example as shown in FIGS. 3-5, the sub-frame 68 is configured to define or carry one or more slide tracks 80 carried on the free end of the sub-frame 68 that is distal or spaced from the table assembly 52. The sub-frame 68 is formed having a plurality of rails 82 that extend lengthwise. The tracks 80 can be formed as an integrated part of the rails 82 or other sub-frame components or can be separately mounted to or supported by the rails. One or more trucks or carriages, hereinafter a sled assembly 86, is mounted on or supported by the sub-frame 68 and is slidable along the tracks 80.

As depicted in FIGS. 2, 3, and 5, the right leg portion 66 further includes a tibia positioning assembly 90 that is mounted on the sub-frame 68. In this example, the tibia positioning assembly 90, or at least a portion of the assembly, is carried on the sled assembly 86. Thus, the tibia positioning assembly 90, or at least a portion thereof, is slidable lengthwise along the tracks 80 of the sub-frame 68 on the sled assembly 86, and thus is movable relative to the table assembly 52 and/or to the thigh immobilizers 70 and knee stabilizers 74.

Figure 6:
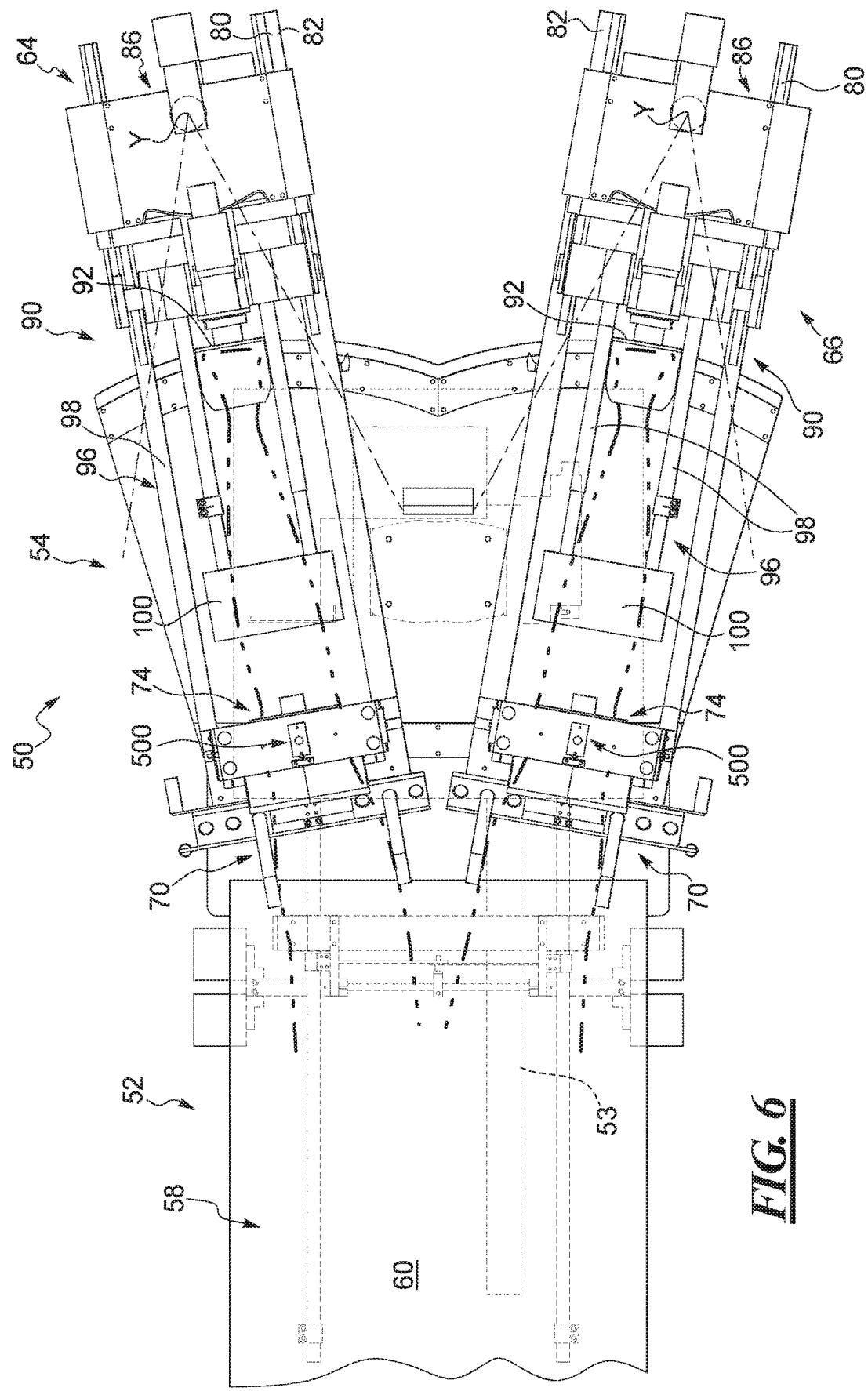
FIG. 6 shows a top view of the robot of FIGS. 2 and 5 and illustrates Varus-valgus motion about the Y-axis of the tibia positioning assembly of each of the left and right leg portions.

In general, the tibia positioning assembly 90 has a foot holder, i.e., a foot plate 92 in this example that faces toward the thigh immobilizers 70 and knee stabilizers 74. The tibia positioning assembly 90 also has a tibia rod device 96 with one or more rods 98 and a calf plate 100 at or near a distal end of the tibia rod device. The one or more rods 98 can be lengthwise adjustable. In this example as shown in FIGS. 3, 5, and 6, the tibia rod device 96 has two tibia rods 98, each of which has two telescoping and lockable segments that permit length adjustment of the rods 98. The telescoping segments permit adjustable positioning of the calf plate 100 relative to the foot plate 92 to accommodate different sized patients. During use, the calf plate 100 lies under and contacts a patient's calf below the knee and the foot plate 92 bears against the sole of the patient's foot. The foot plate 92 can be configured to physically constrain and hold the foot of a patient against the contact surface 94. In one example, though not shown herein, the foot plate 92 can employ one or more straps that secure the sole of their foot to the foot plate 92. Likewise, the calf plate 100 can be configured to physically constrain the patient's leg to the calf plate, as described below for certain tests, or can merely lie against and under the patient's calf while not being otherwise secured to the leg for other tests.

With reference to FIGS. 3 and 5-7, the tibia positioning assembly 90 has a drive system with a number of drive components configured to impart specific and controllable movements to the lower leg of a patient. The drive system in this example generally has a first drive, i.e., an X-axis drive 104 as identified herein, which is oriented to define and provide rotation about a first axis, i.e., an X-axis as identified herein, which in this example lies generally laterally across the tibia positioning assembly 90. The drive system also has a second drive, i.e., a Y-axis drive 106 as identified herein, which is oriented to define and provide rotation about a second axis, i.e., a Y-axis as identified herein, which in this example lies generally vertically through the tibia positioning assembly 90, though not quite intersecting the X-axis, as described below. The drive system further has a third drive, i.e., a Z-axis drive 108 as identified herein, which is oriented to define and provide rotation about a third axis, i.e., a Z-axis as identified herein, which in this example lies lengthwise along the tibia positioning assembly 90. The three axes define a coordinate system and this coordinate system is identified as an X-Y-Z coordinate system for the right leg portion 66 of the robot 54 in this example. The robot 54 will also have a similar X-Y-Z coordinate system specific to the left leg portion 64, but independent of the coordinate system for the right leg portion 66.

In other examples, the RKT apparatus may be configured to test only one or two of anterior-posterior motion, Varus-valgus motion, or tibial rotation, instead of all three tests. In such cases, the drive system may include only one or two of the X-axis, Y-axis, or Z-axis drives instead of all three drives. The methods and procedures described herein may be modified to accommodate such robots that have fewer than all three drives. In other examples, the X-Y-Z axes of the aforementioned coordinate systems may all intersect with one another and may all be orthogonal to one another. In still other examples, none or only two of the axes may intersect and/or none or only two of the axes may be orthogonal to one another.

Though not described in detail herein, the X-axis drive 104 can include a first motor, such as an electric motor, a gearbox, and an output shaft that is driven by the motor and gearbox. Opposite ends of the output shaft in this example are fixedly coupled to the upper ends of respective drive links 116 on opposite sides of a housing 102 that encloses the motor, gearbox, and shaft. The lower end of one of the drive links 116 is coupled or fixed to an X-axis torque transducer 118. The torque transducer 118 is also coupled or fixed to an element coupled to fixed segments of the tibia rods 98, as shown in FIGS. 3 and 5.

With reference to FIG. 5, the X-axis drive 104 is configured to conduct an anterior-posterior or A-P test on a patient's knee. Position sensors can be applied to appropriate locations on the right leg of the patient. The X-axis drive 104 imparts force about the X-axis to initiate anterior-posterior motion in the tibia part of the knee joint relative to the fixed femur part of the knee joint of the patient, as shown in FIG. 5. The motor can reversibly rotate the output shaft through an arc about the X-axis whereby the upper ends of the drive links 116 are rotated through the same arc. This in turn moves, i.e., raises or lowers the lower ends of the drive links 116, which in turn raises or lowers the tibia rods 98. Movement of the tibia rods 98 raises or lowers the calf plate 100 carried on the tibia rods. The X-axis torque transducer 118 measures the applied torque caused by the load applied at the calf plate 100 as the calf plate pushes up on the patient's tibia or the tibia rods 98 pull down on the patient's tibia. Motion and load data can be collected by a processor from the sensors relative to the motion in the patient's leg and from the X-axis torque transducer 118 relative to the torque or applied force.

The above-described anterior-posterior movement components of the tibia positioning assembly 90 can vary considerably from the example shown and described herein. Likewise, the configuration and construction of the drive links 116, tibia rods 98, and calf plate 100 can also be varied. The mechanisms or devices that are used to secure a patient's leg to the tibia rods 98 and to the foot plate 92, if and when needed for testing, can also vary.

Figure 7:
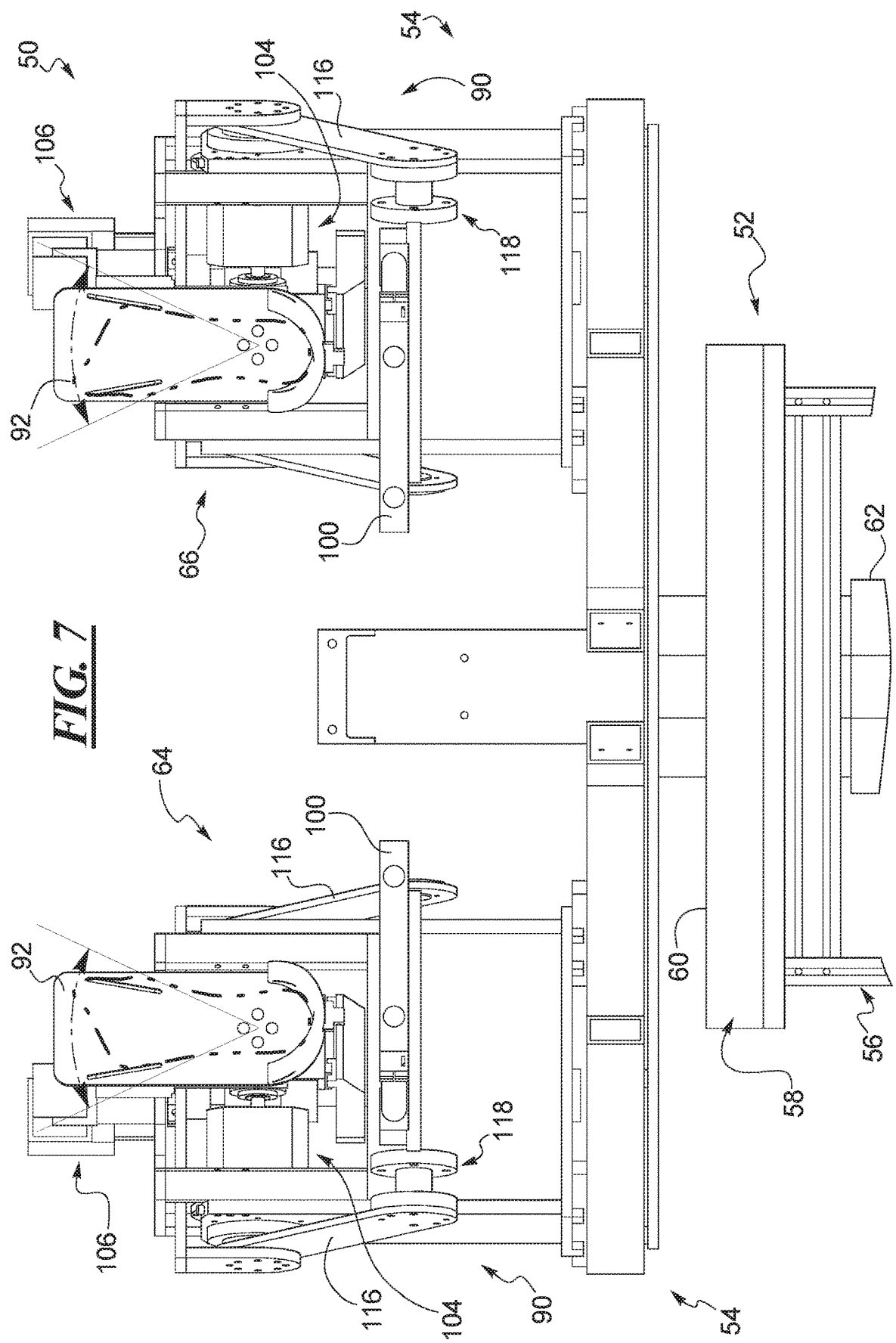
FIG. 7 shows an end view of the robot of FIGS. 2 and 5 as viewed from the left-hand side in FIG. 1 and illustrates internal and external rotation about the Z-axis of each of the left and right leg portions.

As shown in FIGS. 3, 6, and 7, the Y-axis drive 106 can include a second motor, which can also be an electric motor, a gearbox, and an output shaft that is driven by the motor and gearbox. A Y-axis torque transducer 148 is fixed to the output shaft for rotation therewith about the Y-axis. As shown in FIG. 6, the Y-axis drive 106 is configured to conduct a Varus-valgus or V-V test on a patient's knee. Position sensors can be applied to appropriate locations on the right leg of the patient. The Y-axis drive 106 imparts force about the Y-axis to initiate Varus-valgus motion in the tibia part of the knee joint relative to the fixed femur part of the knee joint of the patient, as shown in FIG. 6. The motor can reversibly rotate the output shaft through an arc about the Y-axis. The Y-axis torque transducer 148 measures the applied torque at the output shaft caused by the load applied to the foot plate 92 as the foot plate 92 pushes the patient's tibia medially or laterally relative to the femur. Motion and load data can be collected by a processor from the sensors relative to the motion in the patient's leg and from the Y-axis torque transducer 148 relative to the torque or applied forces.

The above-described Varus-valgus movement components of the tibia positioning assembly 90 can also vary considerably from the example shown and described herein. The mechanisms or devices that are used to secure a patient's leg to the tibia rods 98 and to the foot plate 92, if and when needed for testing, can also vary.

As shown in FIGS. 3 and 7, the Z-axis drive 108 can include a third motor, which can also be an electric motor, a gearbox, and an output shaft that is driven by the motor and gearbox. The Z-axis drive rotates the footplate 92 about the Z-axis when conducting a rotation test on a patient's knee. A Z-axis torque transducer 168 is fixed to the output shaft of the Z-axis drive 108 for rotation therewith. The foot plate 92 is secured to the torque transducer 168 for rotation therewith. Thus, as the output shaft is reversibly rotated by the motor and gearbox about the Z-axis, as shown in FIG. 7, the foot plate 92 will all rotate about the Z-axis.

As represented in FIGS. 3 and 7, the Z-axis drive 108 is configured to conduct an internal and external rotation test or simply a tibia rotation test on a patient's knee. Position sensors can be applied to appropriate locations on the right leg of the patient. The Z-axis drive 108 imparts force about the Z-axis to initiate rotation motion in the tibia part of the knee joint relative to the fixed femur part of the knee joint of the patient, as shown in FIG. 7. The motor can reversibly rotate the output shaft through an arc about the Z-axis whereby the torque transducer 168 is rotated through the same arc. This in turn moves, i.e., rotates the foot plate 92 about the Z-axis. Movement of the foot plate 92 in this manner rotates the patient's lower leg internally and externally relative to the femur. The Z-axis torque transducer 168 measures the applied torque caused by the load applied at the foot plate 92 as the foot plate rotates. Motion and load data can be collected by a processor from the sensors relative to the motion in the patient's leg and from the Z-axis torque transducer 168 relative to the torque or applied forces.

The above-described rotation movement components of the tibia positioning assembly 90 can also vary considerably from the example shown and described herein. The mechanisms or devices that are used to secure a patient's leg to the foot plate 92, if and when needed for testing, can also vary.

In use, a patient lies on the padded surface 60 of the patient platform 58 on the table assembly 52 as shown in FIG. 2. The patient's knees are positioned to engage the knee stabilizers 74, their thighs are positioned to engage the thigh immobilizers 70, their feet are positioned to engage the foot plates 92, and their calves are positioned to engage the tibia rods 98. The patient can then be secured to the foot plates, to the knee stabilizers, and to the thigh stabilizers for testing and evaluation. The patient's calves or tibias can also be secured to the tibia rods 98 and/or the calf plates 100, as needed for specific testing. Movement of the lower leg of the patient may be detected by non-invasive systems utilizing sensors or markers that are attached to the skin, including but not limited to optoelectronic, ultrasonic, and electromagnetic motion analysis systems. In one example, the RKT apparatus 50 can be configured so that the patient's knees are flexed to about 30 degrees between the femur and the tibia. However, the tests or evaluations may also include the additional capability to flex the knee from 0 to 90 degrees to allow for similar tests (such as the examples above) done for different degrees of knee flexion.

Any one of the X-, Y-, and Z-drives can be decoupled from any of the other two. In the disclosed example, each of the three drive assemblies may be operable with one or more of the other at the same time or can be decoupled from each of the other two and be operable independent of the other two. In other examples, two or more, and perhaps all three of the drives can be mutually coupled relative to one another such that movements are substantially simultaneously imposed upon the patient's legs during use of the RKT apparatus.

The aforementioned sensors can be provided on the legs of a patient, in the power lines of the RKT apparatus, and/or on the X-, Y-, and Z-drives to obtain desired position or location data as the lower leg is moved during testing and evaluation. The degree of movement of the patient's legs in the A-P test, the V-V test, and/or the rotation test can be measured by detecting the movements of the parts of the apparatus, the rotation of the drives, and/or the actual movements of the patient's legs. The torque encountered during each test and over the range of motion applied during each such movement may also be measured, suitably calibrated to the limb movement, and recorded.

As noted above, even testing and evaluation of knee joints using the RKT apparatus 50 can be inconsistent from patient to patient, from doctor to doctor, and from test procedure to test procedure by the same doctors and/or on the same patients. Such inconsistency is created at least in part because each stage or step of the setup and testing procedures can introduce error into the data. Such inconsistency may also be caused in part by residual movement of the patient's femurs, which are retained by the thigh immobilizers 70 and knee stabilizers 74. The cumulative error can become quite substantial and thus significantly affect the accuracy of the test results. As disclosed herein, important stages or steps for each test are patient set-up and robot set-up. Further, according to the teachings of the present disclosure, detecting and accounting for residual movement of the patient's femur during testing can reduce cumulative error. Also, providing a consistent method or procedure to get a patient set-up in the RKT apparatus 50 has been determined to aid in producing more consistent test results and reducing error in the data. Further, providing a consistent method or procedure to set up or initialize the robot 54 of the RKT apparatus 50 prior to testing a given patient has also been determined to aid in producing more consistent test results and reducing error in the data.

Figure 8:
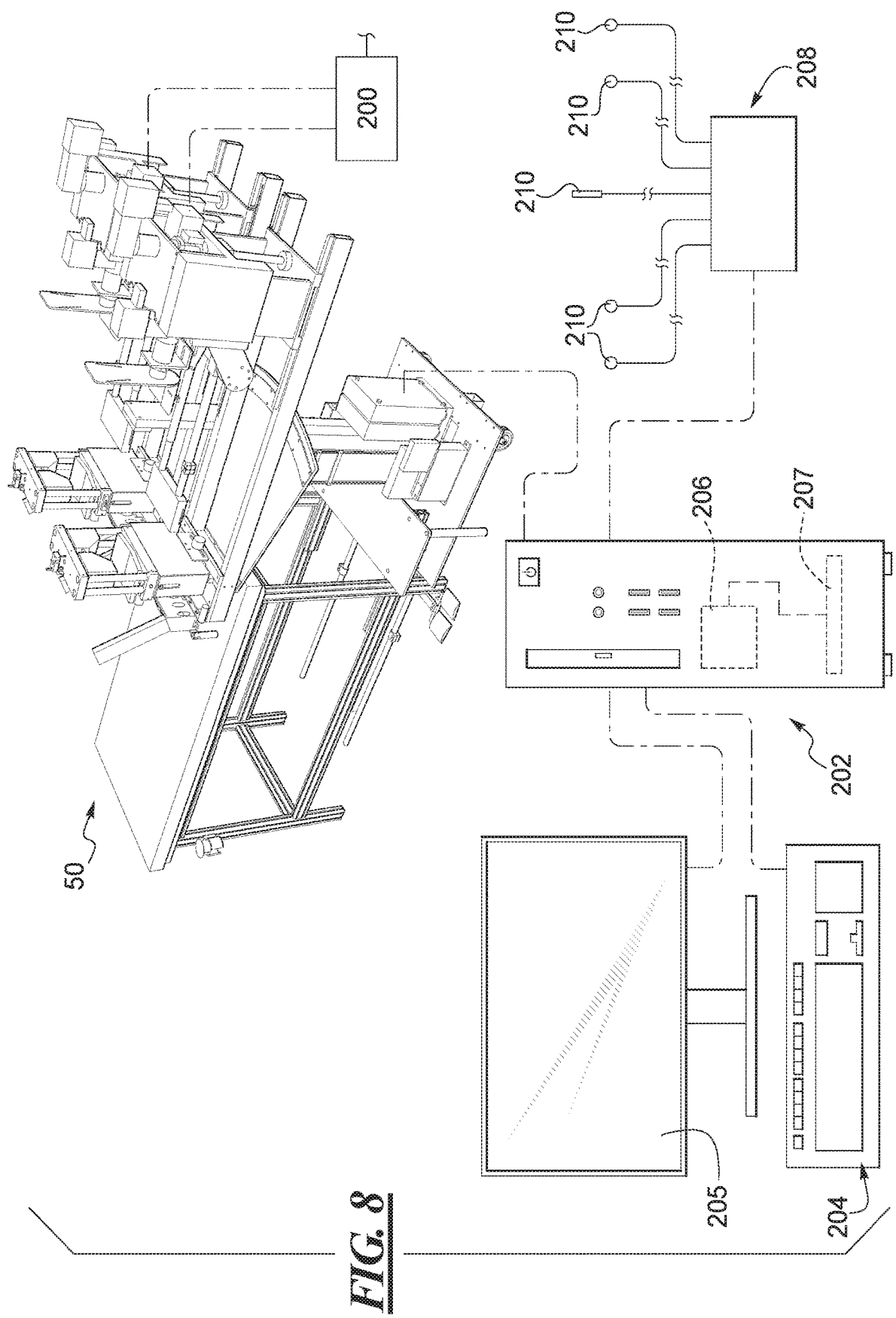
FIG. 8 shows an environment view of a system utilizing the RKT apparatus of FIG. 1.

As shown in FIG. 8, the robot 54 of the RKT apparatus 50 can be part of a system and connected to a power source 200 to operate the robot. The power source 200 can be a typical 120/220 volt AC grid, a converted direct current power source, a stand-alone power source such as a generator or battery, or the like. The robot 54 of the RKT apparatus 50 can also be connected to a programmable electronic device or network of devices, such as a computer 202 or a computer network, a network server, or the like that are part of the system. In any case, the computer 202 can have or can be connected with an input device 204, such as a keyboard, a user display 205, such as a monitor or screen, a memory 206, and a processor 207. The robot 54 and/or computer 202 can also be coupled to a sensor or tracking system 208. The tracking system 208 can utilize one or more individual sensors 210 that are configured to detect or determine spatial positioning or location of the sensor at a point in time. The types of sensors 210 and tracking system 208 can employ electromagnetic (EM) sensors, electromagnetic field (EMF) sensors, or other suitable sensor technology.

In the disclosed example, the X-, Y-, and Z-drives 104, 106, 108 can be connected to and operable by the computer 202. The computer 202 can be programmed to receive and store load or torque data from the X-, Y-, and Z-drives 104, 106, 108 and to receive and store spatial position data from the sensors 210 and tracking system 208. The processor 206 can be programmed to calculate information and provide feedback related to knee laxity, based on the data. The information and feedback can be provided to the examiner on the display 205. The knee laxity information and feedback can relate to anterior-posterior movement, Varus-valgus movement, and/or tibia rotation movement, as described above. As represented in FIG. 9, the set-up of the patient relative to the RKT apparatus and particularly the robot 54 can be performed or specified as disclosed herein to aid in rendering the test data, information, and feedback more consistent and more accurate. Likewise, also as shown in FIG. 9, the set-up of the robot 54 prior to undertaking any testing can also be performed or specified to aid in rendering the test data, information, and feedback more consistent and accurate.

FIG. 10 shows a block diagram that is representative of a set-up method according to the teachings of the present disclosure. In this example, the method combines steps relating to setting up the patient relative to the RKT apparatus and setting up the robot 54 prior to testing. In other examples, the method may include only steps to set-up the patient relative to the RKT apparatus 50 and robot 54. Likewise, the method may include only steps to set up the robot 54 prior to testing.

Figure 12:
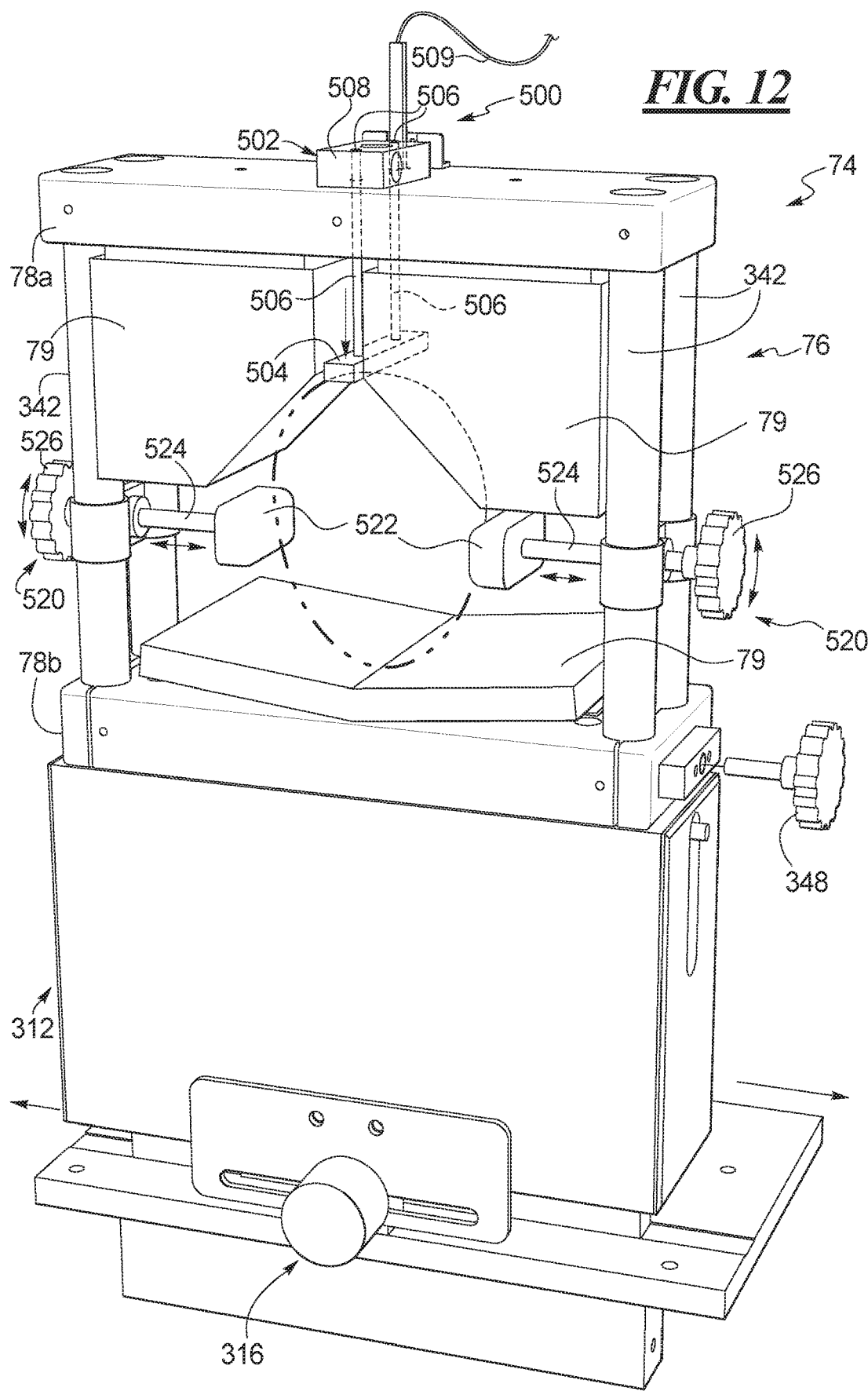
FIG. 12 shows a patella sensor of the knee stabilizer of FIG. 11 in contact with the leg of the patient.

With reference to FIG. 12, at block 300, the RKT apparatus 50 is turned on or powered up. In the disclosed example, to do so, the computer 202 including the applicable program, the tracking system 208 including the sensors 210, and the robot 54 are each started, turned on, or powered up. The objective of this step is to get the RKT apparatus up and running and to prepare the apparatus for use.

At block 302, the drives or motors of the robot 54 are leveled. In the disclosed example, to do so, the motors of the corresponding X-, Y-, and Z-drives 104, 106, 108 can be precisely leveled relative to a horizontal or vertical reference or referencing a leveling device. In one example, a portion of the tracking system 208 can be used to precisely level the motors. Alternatively, the motors can be leveled manually or mechanically such as by using an inclinometer. The objective of this step is to provide and define a consistent, repeatable starting point for the tibia positioning assembly 90 that can be achieved prior to each test using the RKT apparatus 50.

At block 304, the torque in each of the drives or motors is zeroed. In the disclosed example, to do so, each of the motors of the drives 104, 106, 108 is zeroed. The motors may thus be adjusted, positioned, or re-set to a condition where the torque transducers read zero torque or where the output shafts are under no torque. The objective of this step is to provide and define a consistent and repeatable starting condition, i.e., a neutral or zero torque starting point for each drive or motor prior to each test using the RKT apparatus 50.

At block 306, the positioning system 53 is utilized to aid or assist a patient in getting up onto the table assembly 52 and in positioning the patient's lower extremities or lower legs relative to the robot 54 for testing and evaluation. In the disclosed example, the positioning system 53 and the robot 54 can be moved to an extended position slid away and spaced from the distal edge of the table assembly 52. The patient can then be situated in an upright position between the robot 54 and the table assembly 52. The patient can then step up on the step 57, if needed, onto and then lie down on the table assembly 52. The robot 54 can be returned toward and beneath the patient's legs. The objective of this step is to make it easy for most patients to get up onto the table assembly 52 for testing.

At block 308, the abduction angle of the patient's femurs is adjusted relative to their hips. In other words, the patient moves or is positioned on the table assembly 52 and on or in the tibia positioning assemblies 90 so that their femurs are at a desired abduction angle. This adjustment can be done in order to adjust the abduction angle of the patient's femurs so that their femurs are neutrally aligned with their hips. Alternatively, and in this example, the tibia positioning assemblies 90 may be in a fixed abduction orientation, such as at a fixed 30-degree angle relative to one another, as noted above. The thigh stabilizers 70 may then be adjustable laterally as mentioned further below so that the patient's femurs can be neutrally aligned with their hips. The objective of this step is to position the patient's femurs in a consistent, repeatable, and comfortable manner relative to the robot 54. The desired position is to have the femurs neutrally lined up with the patient's hips so as to limit stress on the patient's upper legs and hips during a test and to create a repeatable and consistent orientation of the lower legs relative to the femurs of the patient.

At block 309, the position of the robot 54 is adjusted relative to the patient's trunk and table assembly 52 in the horizontal and vertical direction using the positioning system 53 to position the patient's knees in a desired degree of flexion. Here, the vertical movement of the column lift 62 and horizontal movement of the positioning system 53 may be done simultaneously or independently to adjust the degree of flexion in the patient's knee. The objective of this step is to allow the clinician to position the patient's knees in the desired flexion in a range of 0 to 90 degrees.

At block 310, the patient's knees are centered relative to the respective knee stabilizers 74. In the disclosed example, as shown in FIGS. 3-5, each knee stabilizer 74 is mounted on or to a support base 312, which is positioned under and coupled to the lower knee clamping element 78b and attached to the guide rails 82. The upper knee clamping elements 78a may be removed for this step. The support base 312, and thus the knee stabilizer 74, is side-to-side adjustable. The knee stabilizer 74 can incorporate a locking element 316 that is configured to selectively secure or release the knee stabilizer 74 relative to the slide track. In the disclosed example, to center the knee stabilizers 74 on the patient's knees, one can release the locking elements 316 and slide the knee stabilizers side-to-side. The knee stabilizers 74 can be moved to laterally center the corresponding posterior knee pads 79 on the lower knee clamping elements 78b under the knees of the patient. The construction of the support base 312 and locking elements 316 can vary considerably and still function as intended to provide side-to-side adjustability of the knee stabilizers 74. One objective of this step is to define a consistent and repeatable position for the patient's knees relative to the tibia positioning assemblies 90 generally in the X-axis direction. Another objective of this step is to center the patient's knees within the knee stabilizers 74 so that, when ultimately clamped onto the knees of the patient, each knee is centered among the pads 79 and thus securely retained in position to inhibit movement of the femur and patella once clamped in the respective stabilizer.

At block 320, the thigh immobilizers 70 are adjusted to secure the patient's femurs in place. In the disclosed example, as shown in FIG. 4, each thigh immobilizer 70 has a primary mechanical adjustment device. Each thigh immobilizer 70 is mounted to a support block 325 carried on a plate 322 attached to the guide rails 82. Each thigh immobilizer 70 may also include a locking mechanism 326 for each of the clamping elements 72. Each clamping element 72 has a truck 324 that carries a paddle 73 extending upward from the truck. In the disclosed example, the clinician can release the locking mechanisms 326 and slide the thigh clamping elements 72 and trucks 324 laterally and independent of one another. The construction of the locking mechanisms 326 can vary considerably and still function as intended to provide side-to-side independent adjustability of the thigh clamping elements 72 on each of the thigh immobilizers 70. The trucks 324 and thigh clamping elements 72 can optionally include a secondary distinct mechanical adjustment device as well. This feature can aid in allowing the thigh immobilizers 70 to accommodate a wider range of patient leg sizes from small children to large adults. In this example, each truck 324 has multiple bores 337 that are laterally spaced apart and open to the top surface of the truck. Each paddle 73 has a corresponding peg or pin 334 protruding downward from the body of the paddle. The peg 334 of each paddle can be selectively inserted into any one of the multiple bores 337 in the corresponding truck 324. By choosing different arrangements of the bores 337, and without moving the trucks 324, the adjacent paddles on one of the thigh immobilizers 70 can be mounted to the trucks 324 in a plurality of different positional arrangements. Depending on which of the bores 337 are selected, the paddle spacing can be altered and/or the paddles can be shifted to the left or to the right, if desired or needed, also without having to move the trucks 324. This secondary adjustment scheme allows for greater versatility in setting up a patient. Any type of locking mechanisms, such as a cam lock type device, can be used to also secure the pegs 334 in the bores 337, if desired, or a separate retention means, if any, may also be used to retain the paddles to the trucks 324.

Once the patient's knees are correctly positioned, according to the step at block 306, and the knee stabilizers 74 are centered according to the step at block 310, the thigh immobilizers 70 can be adjusted, set, and clamped onto the patient's thighs. Each thigh clamping element 72 should be positioned or secured such that the medial and lateral clamping elements apply substantially equal pressure to the thigh. One objective of this thigh clamping step is to permit a consistent and repeatable position for the patient's thighs relative to the tibia positioning assemblies 90, also generally in the X-axis direction. Another objective of this thigh clamping step is to then securely clamp the patient's thighs in place with the thigh immobilizers 70. During testing, it is desirable that the femur position for each leg of a patient is securely retained to prevent lateral movement and femoral rotation once the thigh immobilizers 70 are adjusted and locked in place.

At block 340, each knee stabilizer 74 is clamped onto the patient's knee or patella. In the disclosed example, as depicted in FIGS. 3-5, the framework 76 of each knee stabilizer 74 can include a pair of guide posts 342 on each side of the stabilizer. The guide posts 342 can be fixed to the upper knee clamping element 78a and can depend down from the element. Free ends 344 of the guide posts can be received in and slide through a corresponding pair of holes 346 on each side of the lower knee clamping element 78b. The upper and lower clamping elements 78a, 78b are adjustable vertically relative to each other, as noted above, by sliding the upper clamping element 78a and guide posts up and down relative to the lower clamping element 78b, which is fixed to the support base 312. A fixing screw 348 in this example extends transversely into each side of the lower clamping element 78b between the pair of holes 346. The fixing screw 348, when rotated in one direction can reduce the diameter of the holes 346 to clamp onto and lock guide posts 342 and, when rotated in the opposite direction, can increase the diameter of the holes to release the guide posts. With the guide posts 342 released, the upper knee clamping elements 78a (and guide posts 342) can be removed from the lower knee clamping element 78b so that the patient's knees can be readily positioned on the lower clamping elements, as noted for the step at block 306. Once the knees are properly positioned after the step at block 306, the upper knee clamping element 78a can be replaced on the lower knee clamping element 78b any time before block 340.

At this point, the locking elements 316 on the knee stabilizers 74 are still released so that the knee stabilizers 74 are free to slide or move laterally. Also at this point, the upper knee clamping element 78a should now be or should already have been reinstalled on the lower knee clamping element 78b. The upper knee clamping element 78a is then clamped downward so that the pads 79 on the upper knee clamping element press down against the patella of the knee. The downward clamping force should achieve a predetermined or desired force, such as 30 lbs., and equal pressure should be applied to both the medial and lateral sides of each knee stabilizer 74. The knee stabilizers 74 can then be secured in this clamping condition. In this example, the fixing screws can be rotated to secure the guide posts 342. A force gage or other suitable method and/or device can be used to achieve the desired downward clamping force applied by the knee stabilizers 74 on each patella of the patient. Once the knee clamping elements 78a are clamped and locked, the knee stabilizers can then be locked in place laterally by actuating the locking elements 316. The objective of this knee clamping step is to securely clamp the patient's knee at the patella in the knee stabilizers 74. During testing, it is desirable that the lower end of the femur and the patella are securely retained to prevent vertical movement at the patella once the knee stabilizers 74 are adjusted, clamped down, and locked.

At block 350, the patient's feet are placed against the foot plates 92. In the disclosed example, the tibia positioning assemblies 90 are drawn toward the patient's feet by sliding the assembly along the tracks 80 on the sub-frames 68. Once the feet are in contact with the two foot plates 92, the tibia positioning assemblies 90 are in a testing position relative to the patient's feet and lower legs. When the feet are properly positioned, appropriate straps (not shown) can be used to secure the feet to the foot plates 92. One objective of this step is to provide a consistent and repeatable mechanism to properly position the tibia positioning assemblies 90 along the sub-frames 68 relative to a specific patient. Another objective of this step is to secure the patient's feet to the foot plates and thus to the drive system of the tibia positioning assemblies.

At block 360, the tibia positioning assemblies 90 are locked in place. In the disclosed example, each tibia positioning assembly 90 can be locked in the set or adjusted position that is achieved at the step of block 350. This will lock the tibia positioning assemblies 90 at the adjusted position accommodating the particular patient being set up. A ruler 362 or other indicia or markings may be provided on or along one of the lengthwise parts of each sub-frame 68, such as along one of the rails 82 (see FIG. 5). The rulers 362 can be configured to identify the length of the lower legs of the patient being set up, based on the position of the tibia positioning assemblies 90 along the tracks 80 or the sub-frames 68. This measurement can be recorded for each specific patient and can then be utilized to set up the robot 54 for a particular patient each time the patient is tested. This helps to ensure that the RKT apparatus 50 is set up the same way for the same patient each time the patient is tested. The objective of this step is to aid in providing a fixed, consistent, and repeatable set-up position for the tibia positioning assemblies 90 for each patient.

At block 370, the patient's feet are rotated to a desired initial rotational orientation. In the disclosed example, each foot plate 92 can be manually rotated to a desired position determined by the orientation of a part of the patient's foot or a part of the foot plate. For example, the patient's foot could be positioned with the toes up and perpendicular to the floor beneath the RKT apparatus. More specifically, the starting orientation may be to orient the second toe on each foot point vertically perpendicular to the floor. This initial foot rotation position can instead be established by moving the Z-axis motor into a neutral zero-torque position to find a true resting position for the patient's feet. The objective of this step is to define a consistent and repeatable starting orientation for the foot plates 92.

At block 380, each tibia rod device 96 is properly positioned under the patient's calves. In the disclosed example, each tibia rod device 96 can be length adjustable to retract or extend the calf plate 100 to a desired position under the corresponding calf of the patient. Once in the desired position, the calf plate is in a testing location or an AP test location relative to the patient's leg. A ruler or other indicia or markings (not shown) may be provided along part of the tibia rod device 96 to help determine the proper or desired position for the calf plate 100 (see FIG. 5). If the desired positon of the calf plate 100 for each patient is to be three-quarters (¾) of the way up the leg from the patient's heel, the ruler (not shown) can be a ¾ scale version of the ruler 362, which defines the patients leg length. Thus, by selecting the same measurement on both rulers 362, the position of the calf plate 100 is assured on each tibia positioning assembly 90 for each patient. Such measurements help to ensure that the patient set-up is as consistent as possible. The objective of this step is to provide a mechanism to ensure repeatable and consistent positioning of the tibia rod device 96 so that the AP test is always conducted at the same relative location on each patient's legs.

At block 390, tibial sensors 210 are placed on the patient's legs. In the disclosed example, sensors 210 are positioned on the flat region of the bone that is just medial to the tibia tubercle on each leg. The sensors 210 are then strapped into place at this location. The location is selected for the sensors 210 because this region has the least amount of soft tissue between the sensor and the bone. This location will thus help during testing to limiting the degree of movement of the sensors caused by the soft tissue moving relative to bone. In one example, round sensor holders can be used to retain each sensor 210 in order to inhibit or prevent the sensors from rocking, due to compression of the calf muscle during testing.

At block 400, the desired test or tests are then conducted on the patient that has been set up in the RKT apparatus 50. These tests can include the anterior-posterior or AP test, the Varus-valgus or V-V test, and the medial and lateral rotation test. Data is collected during the testing by the computer and can be evaluated by the computer in order to render a diagnosis for the knee joint being tested with respect to knee laxity and joint play.

Additional set-up procedures may be utilized during testing or prior to testing in addition to those discussed above. For example, during AP testing, one or more straps may be utilized to secure the patients legs to the tibia rod devices 96. This may be to ensure that the tibia rod devices can both push up in an anterior direction on the patient's legs and pull down in a posterior direction on the patient's legs during testing. Once the AP test is completed, these straps may be removed and the tibia positioning rods can be moved out of the way prior to conducting a rotation test or a Varus-valgus test on the patient. In another example, during a Varus-valgus test, additional pads can be pushed into the knee stabilizers 74 between the medial and lateral sides of the patient's knees and the framework 76. Such pads may help to minimize medial or lateral movement of the knee under the clamp and minimize axial rotation during the Varus-valgus test. Alternatively, the knee stabilizers can be fitted with additional elements, such as adjustable medial and lateral constraints (to replace the additional pads) and/or a patella sensor to further eliminate error during testing, as described below. These added features can further reduce error in the collected data.

In one example, it may be understood that during the above tests (AP, Varus-valgus, or rotation), the knee is flexed to about 30 degrees. However, the tests or evaluations may also include the additional capability to flex the knee from 0 to 90 degrees to allow for similar tests (such as the examples above) done for different degrees of knee flexion.

As a bone, the femur is encased in soft tissue such that a sensor on the skin will not follow its motion. To get around this problem, the joint stabilizer, which is the knee stabilizer 74 in this example, is intended to rigidly clamp the femur through the soft tissue to the RKT apparatus 50 during testing. The knee stabilizer 74 pushes the patella down into the groove of the trochlea helping to lock the femur in rotation. The pads 79 of the knee stabilizer 74 may allow 30 lbs. force of compression while maintaining the patient in a reasonable comfort zone. Once the patient's leg is secured or clamped by the knee stabilizer 74, it was assumed that the femur does not move and a device based coordinate system is developed as the femoral coordinate system for testing and evaluation.

The applicant, however, has discovered that, during testing, a patient's patella can move rather substantially, even with the knee joint and femur held stationary by the knee stabilizer 74. The problem is that during the anterior/posterior or AP test, further compression of the pads 79 occurs, which allows an anterior/posterior translation of the femur to occur. This translation of the femur is added to the translation of the tibia. Since the clinician is only interested in the translation of the tibia, this residual translation of the clamped femur is a problem. The residual translation can hinder the accuracy of the data retrieved.

The solution to the problem was developed by the applicant in the form of a "floating" sensor system 500, as shown in FIGS. 1-5, that sits on top of the patella and floats with the patella through the knee stabilizer 74. The sensor system 500 includes a floating sensor element, which is shown in the upper knee clamping element 78a of FIGS. 11 and 12. The disclosed sensor system 500 can measure and account for the residual translation of the femur in the data, providing "true" test results, thus representing the true anterior/posterior position of the femur during the test. The true position can then be used to develop the device-based femoral coordinate system, resulting in more accurate test and evaluation data. Residual anterior and posterior translation of the femur during the test caused by compression of the pads within the clamp is accounted for in the analysis. Thus, true tibial anterior-posterior translation is identified.

Figure 11:
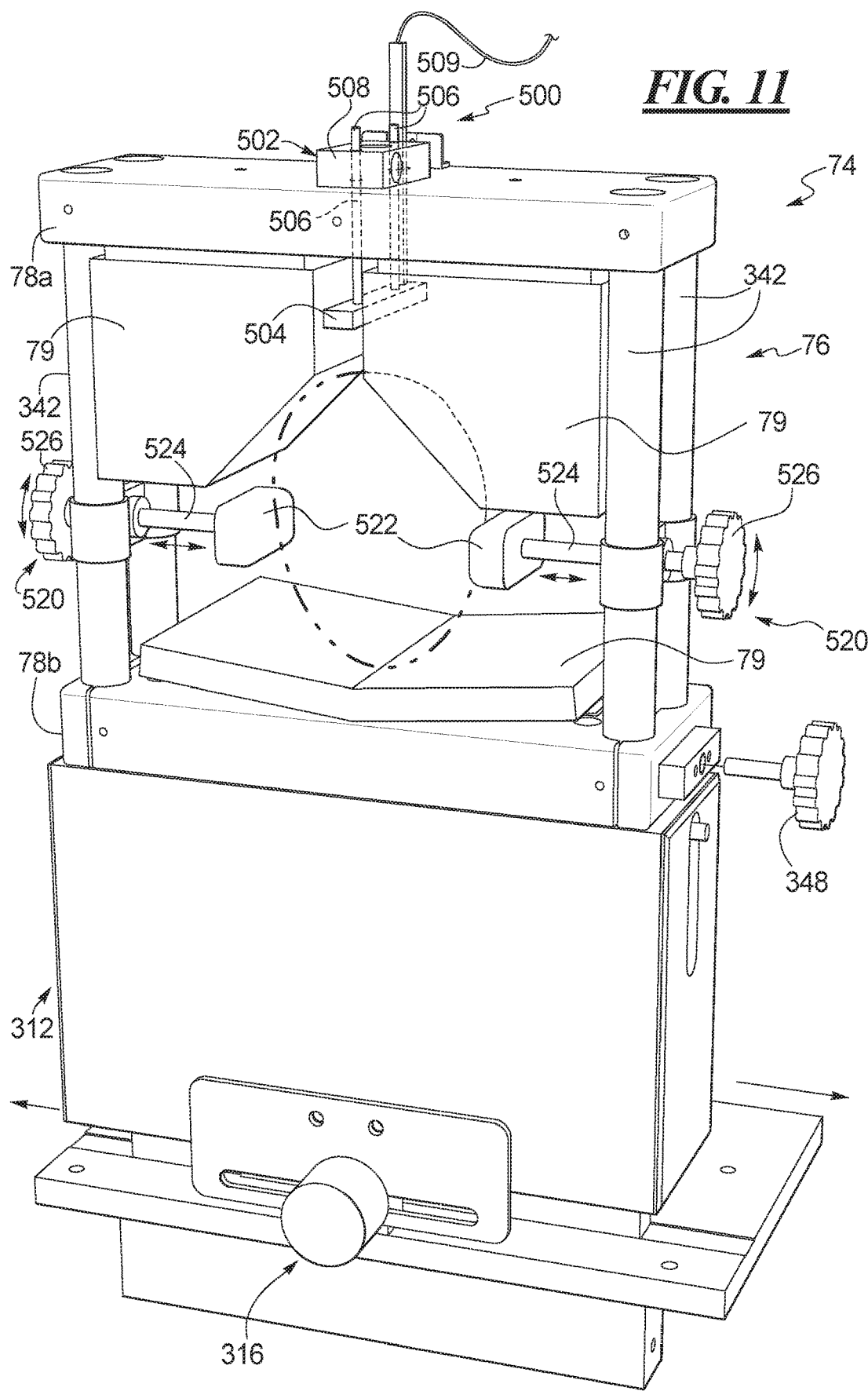
FIG. 11 shows the knee stabilizer of the right leg portion of FIGS. 3 and 4 and with a leg of a patient depicted within the knee stabilizer, and depicts optional medial and lateral constraints attached thereto.

With reference to FIGS. 11 and 12, the sensor system 500 in this example includes an electromagnetic sensor 502 that has a joint contacting end 504, which can be a plastic part, and which can rest via gravity (FIG. 12) on top of the patella. Rods 506 are attached to the joint contacting end 504 and extend through the upper knee clamping element 78a of the knee stabilizer 74. The rods 506 can then be connected to an electromagnetic sensor body 508 that is carried on the upper knee clamping element 78a or another part of the knee stabilizer 74. A linear bearing (not shown) may also be incorporated into the system so that the rods 506 can slide along only one linear axis or in one dimension, the anterior/posterior or AP dimension, relative to the sensor body 508. It has been determined that the majority of residual femur motion within the knee stabilizer 74 during testing is in the AP direction. Thus, in one example, the floating sensor 502 can be configured to account for translation in only one direction or axis, such as the AP direction.

The disclosed floating sensor design or system 500 may include only materials that would not interfere with the electromagnetic system of the RKT apparatus or a CT scanner in which the apparatus might be placed during testing. In one example, the sensor system 500 components can include a plastic body or contacting end, brass rods, and stainless steel components. Aluminum could also be used. The floating sensor system 500 can include a lead 509 that connects the system to the computer 202 of the RKT apparatus system. Thus, data form the floating sensor 502 can be collected during testing to account for the undesirable residual femur translation.

In the above-discussed set-up procedures, at block 510, after the patient's knees are clamped at block 340, the floating sensor system 500 can be zeroed out to determine the nominal unstressed position of the patient's femur. This step at block 510 can also optionally be done after: i) the feet are secured at block 350; ii) the tibia positioning assemblies 90 are fixed at block 360; iii) the zero-rotation position of the tibias are set about the Z-axis at block 370; iv) the tibia rod device 96 length is set at block 380, or v) the sensor 210 are put in place at block 390.

As noted above and as shown in FIGS. 11 and 12, the knee stabilizers 74 may also optionally include mechanical, adjustable medial and lateral constraints 520 coupled to the sides of the stabilizer, such as to the guide posts 342. The medial and lateral constraints 520 can be configured to limit motion of the femur in the medial and lateral directions during Varus-valgus testing and evaluation. In one example, the medial and lateral constraints 520 can include adjustable pads 522 that contact the sides of the patient's knee within the stabilizer 74. The lateral constraints can instead be straps that can further tie down the knee joint. In another example, the medial and lateral constraints can be pneumatic bladders. In one example, the residual movement or floating sensor 502 at the top of the knee stabilizer 74 can be configured to detect residual movement of the joint in the AP direction as well as the medial and lateral directions. In another example, one or more separate additional sensors can be utilized and associated with the medial and lateral constraints 520 that can detect residual movement in the medial and lateral directions.

In one example, the medial and lateral constraints 520 can be adjustable to clamp against the sides of the patient's knees. In this example, the pads 522 are carried on threaded rods 524. The rods 524 have an adjustment knob 526 at the ends opposite the pads 522. The knobs 526 can be turned in one direction to tighten the constraints 520 and can be turned in the opposite direction to loosen the constraints. In another example, the rods can be slidable through a one-way clamp or spring device that, in one position, securely restrain the rods and, in another position, release the rods for adjustment.

The medial and lateral constraints 520 can be tightened during set up of the patient and RKT apparatus 50. The constraints can be adjusted, either when the knee stabilizer 74 is clamped to the knee at block 340, or any time thereafter, but prior to testing at block 400.

As noted, one may choose to only measure residual femoral motion in one dimension, i.e., anterior-posterior translation. However, the sensor may be configured to measure such motion in multiple planes or directions. FIG. 13 shows one such example of a portion of a knee stabilizer 530 and sensor system 532. In this example, the sensor system 532 can allow pivotal rotation of the sensor component 534 system relative to the device-based Z-axis and/or axial rotation of the sensor about the Y-axis, as well as AP sliding motion in the Y-axis direction. Motions of the sensor 534 might include: 1) translation only; 2) translation plus rotation about 1 axis, which may be cylinder-like as in FIG. 13; or 3) translation plus a ball and socket joint, which would allow rotation about all axes. The sensor in FIG. 13 could include a ball instead of a cylinder. The contacting end of the sensor can have a non-slip pad or adhesive that would adhere the contacting end to the top of the patella. Translation of the patella medially or laterally would register as rotation at the sensor. This alternative sensor design may only apply to a tibial axial rotation test and the Varus-valgus test.

In another alternative example, a sensor could be adhesively adhered to the top of the patella. However, the connection would have to overcome problems with adhesion. Also, when the sensor is fixed to the patella, testing has shown that the poor skin to bone interface results in extra unexplained noise being introduced into the data. By restricting motion to only one dimension (linear AP direction) or to two dimensions, off axis noise is minimized in the data obtained.

The disclosed joint stabilizer 74 and residual translation sensor system 500 utilize one form of an electromagnetic sensor 502 to detect the residual movement in the joint secured by the joint stabilizer. Other types of sensors, however, can certainly be utilized within the spirit and scope of the present disclosure. Other types and forms of electromagnetic sensors may also be utilized. The intent of the sensor is for the sensor to detect limited residual movement in the joint, which is supposed to be held fast or stationary by the joint stabilizer during manipulation and evaluation using the apparatus. The sensor may also need to be able to send data and/or signals to a computer, processor, memory device, storage device, or the like and/or to accumulate and store data onboard the sensor.

The design configuration of the joint stabilizer can also vary from the examples shown and described herein. The joint stabilizer frame need not be formed of four or 6 pieces and, thus, need not include upper and lower clamping elements 78a, 78b coupled by pairs of guide or adjustment rods 342. Further, the joint stabilizer can aid in more securely retaining the clamped portion of a joint in the medial/lateral directions as well as anterior/posterior directions of the example described above. In one such example, the joint stabilizer can again be a knee stabilizer and can have a clamshell construction with two semi-circular shell sections. Each shell section can carry a portion of a pad, similar to prior examples. The two shell sections can be joined along one edge at a hinge. The opposite edges of the shell sections can be latched to one another and detached from one another to open and close the frame. The hinge(s) and latch(es) can vary considerably in size, shape, form, and function. The shell sections can also vary in shape and size and again can be made from any suitable materials. With the shell closed around a joint, a sensor can be provided on the upper shell section and function as described above to detect residual movement in a joint clamped by the joint stabilizer.

In yet another example of a joint stabilizer within the spirit and scope of the present disclosure, the joint stabilizer can be a folding or foldable knee stabilizer or patellar clamp. Such a stabilizer can have an upper frame section and a lower frame section connected to one another by two spaced apart side frame sections. In this example, the side frame sections can bend, fold, flex, and/or be hinged to permit movement of the lower frame section relative to the upper frame section. Thus, the joint stabilizer can allow for knee flexion during testing and evaluation. The RKT apparatus may be modified from the aforementioned example and/or may be of an alternate design to accommodate testing of a flexed or bent knee. The side frame sections can be flexible and/or employ one or more hinges to permit movement of the lower frame section relative to the upper frame section during testing.

A manual method of testing and determining the clamping or engagement force of a joint stabilizer on a knee joint of a patient can be used during use. In one example, the joint stabilizer can include a simple hanging weight, spring, or screw mechanism that can indicate the applied joint stabilizer force. A simple meter or force sensor can be used to measure and determine such force. Alternatively, the joint stabilizer and/or RKT apparatus can be modified to more consistently and/or automatically determine the joint clamping force being applied to the knee joint of a patient. In one example, one or more pressure sensors can be provided on or within the pads of the joint stabilizer. The sensors can automatically determine the joint clamping force. The sensors can also be coupled to a processor, computer, or the like to provide pressure data automatically. The data can be stored, can be utilized in any force and movement calculations, evaluations, and/or diagnoses, and/or can be visibly displayed as needed.

Other instrumented systems use a rigid pad on the patella but do not clamp the patella down to standardize the position and pressure on the femur. The classic example is the aforementioned Medmetric KT-1000. The pad sits on the top of the patella but does not "float". It provides a rigid point from which to measure the translation. Thus, residual motion of the femur or patella is not accounted for in any data collected.

Many modifications and other embodiments of the disclosed joint or knee stabilizer and RKT apparatus set forth herein may come to mind to one skilled in the art to which this disclosure invention pertains and upon reading this disclosure. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Specific combinations of features, components, aspects, and arrangements of the RKT apparatuses and stabilizers are disclosed herein. However, one having ordinary skill in the art will understand that each feature, component, aspect, and arrangement may be used independently or in other combinations not specifically disclosed.

The patient and methods disclosed herein may vary from the examples shown and described. One or more of the specific steps may be performed as described but in a different order. Specific steps may be eliminated or altered and additional steps may be added. The design of the RKT apparatus may vary considerably from the example disclosed herein. As the design of the robot or apparatus varies, so may the steps vary, the order of the steps change, the number of steps change, and/or the specific details of the steps be altered or modified. The specific designs of the knee stabilizers and thigh immobilizers may change, whether related to how the devices are assembled, constructed, adjusted, locked, released, or the like. Likewise, the specific designs of the axes drives and/or the overall tibia positioning assemblies may also change.

The disclosed set-up procedures have been developed and are being refined to aid in reducing error and inconsistency in the test results and the underlying procedures. Some of the disclosed set-up steps are for setting up the patient position relative to the robot. Some of the disclosed set-up steps are for setting up the robot itself. However, the steps are conceived to aid in rendering the test procedures and results more accurate and more consistent. According to the disclosure, any patient can be set up relative to the robot in substantially the same way as any other patient. This can make knee laxity data acquired for different patients more directly comparable. According to the disclosure, a given patient can be set up relative to the robot in substantially the same way each time the patient is tested. This can make that patient's test results more relevant when comparing one test to the next. According to the disclosure, the robot can be set up using substantially the same procedure for any patient, other than where patient specific settings are known. This can reduce the amount of error that might otherwise be introduced into any given test.

Many modifications to and other embodiments of the disclosed RKT apparatus, components, methods, uses, and the like set forth herein may come to mind to one skilled in the art to which the invention pertains upon reading this disclosure. Therefore, it is to be understood that the inventions are not to be limited to the specific embodiments and combinations disclosed and that modifications and other embodiments and combinations are intended to be included within the scope of the appended claims. Although specific terms are employed herein, they are used in a generic and descriptive sense only and not for purposes of limitation.

Although certain floating patella sensors and systems, and RKT apparatus, systems, methods, and procedures have been described herein in accordance with the teachings of the present disclosure, the scope of coverage of this patent is not limited thereto. On the contrary, this patent covers all embodiments of the teachings of the disclosure that fairly fall within the scope of permissible equivalents.

What is claimed is:

1. A joint manipulation and evaluation apparatus comprising:
    a positioning structure having an adjustable portion and being movable by a drive system to manipulate a first bone of a joint relative to a second bone of the joint;
    a joint stabilizer having a frame arranged to engage the joint and hold the second bone in place as the first bone is manipulated; and
    a sensor coupled to the frame of the joint stabilizer and configured and arranged to float unstressed relative to the frame and contact a surface of the joint via gravity to detect residual movement of a clamped portion of the joint relative to the joint stabilizer as the first bone is manipulated.

2. A joint manipulation and evaluation apparatus according to claim 1, wherein the sensor has a joint contacting end positioned to contact the clamped portion of the joint, and wherein the joint contacting end moves with the clamped portion of the joint to detect the residual movement of the clamped portion.

3. A joint manipulation and evaluation apparatus according to claim 1, wherein the joint stabilizer is a knee stabilizer and the joint is a knee joint, and wherein the joint stabilizer is arranged to hold a femur of the knee joint as a tibia of the knee joint is manipulated and the sensor is arranged to detect residual movement of a patella of the knee joint.

4. A joint manipulation and evaluation apparatus according to claim 1, the drive system of the positioning assembly further comprising:
- a first drive configured to manipulate the first bone relative to the second bone in a first direction;
- a second drive configured to manipulate the first bone relative to the second bone in a second direction; and
- a third drive configured to manipulate the first bone relative to the second bone in a third direction,
- wherein the first, second, and third directions are different relative to each other.

5. A joint manipulation and evaluation apparatus according to claim 1, wherein the frame is arranged to surround the joint and includes one or more pads carried within the frame, the pads positioned so as to be disposed between the frame and the joint.

6. A joint manipulation and evaluation apparatus according to claim 5, wherein the sensor is an electromagnetic sensor carried on the frame.

7. A joint manipulation and evaluation apparatus according to claim 1, wherein the sensor has a joint contacting end positioned within the frame of the joint stabilizer, the joint contacting end being movable relative to the frame.

8. A joint manipulation and evaluation apparatus according to claim 7, wherein the joint contacting end floats along only a single linear axis relative to the frame of the joint stabilizer.

9. A joint manipulation and evaluation apparatus according to claim 7, wherein the joint contacting end floats along at least one linear axis relative to the frame and is pivotable about a pivot point relative to the frame.

10. A joint manipulation and evaluation apparatus according to claim 1, further comprising a processor, a memory device, or both coupled to the sensor and configured to receive and/or store data signals from the sensor that correspond to the residual movement.

11. A joint manipulation and evaluation apparatus according to claim 1, further comprising a processor coupled to the sensor, the processor programmed to evaluate the joint and to account for the residual movement of the clamped portion when evaluating the joint.

12. A joint manipulation and evaluation apparatus according to claim 1, wherein the sensor is a linear actuator.

\* \* \* \* \*